(12) United States Patent
Sugiyama et al.

(10) Patent No.: US 9,592,019 B2
(45) Date of Patent: Mar. 14, 2017

(54) MEDICAL IMAGE PROCESSING APPARATUS AND MEDICAL IMAGE DIAGNOSTIC APPARATUS FOR ASSOCIATING A POSITIONAL RELATION OF A BREAST BETWEEN PIECES OF IMAGE DATA

(71) Applicant: TOSHIBA MEDICAL SYSTEMS CORPORATION, Otawara-shi (JP)

(72) Inventors: Atsuko Sugiyama, Nasushiobara (JP); Katsuhiko Fujimoto, Saitama (JP); Yoshitaka Mine, Nasushiobara (JP); Masahiro Kumakura, Otawara (JP); Ryota Osumi, Nasushiobara (JP); Hiroki Yoshiara, Nasushiobara (JP); Mariko Shibata, Nasushiobara (JP); Toshie Maruyama, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 15 days.

(21) Appl. No.: 14/611,352

(22) Filed: Feb. 2, 2015

(65) Prior Publication Data
US 2015/0221091 A1    Aug. 6, 2015

(30) Foreign Application Priority Data
Feb. 4, 2014    (JP) .................................. 2014-019761

(51) Int. Cl.
*G06K 9/00* (2006.01)
*A61B 6/00* (2006.01)
(Continued)

(52) U.S. Cl.
CPC ............ *A61B 6/463* (2013.01); *A61B 5/4312* (2013.01); *A61B 6/4417* (2013.01); *A61B 6/502* (2013.01);
(Continued)

(58) Field of Classification Search
None
See application file for complete search history.

(56) References Cited

U.S. PATENT DOCUMENTS

| | | | | |
|---|---|---|---|---|
| 6,317,617 B1 * | 11/2001 | Gilhuijs | ................. | A61B 5/055 128/922 |
| 7,615,008 B2 * | 11/2009 | Zhang | ................. | A61B 8/0825 382/128 |

(Continued)

OTHER PUBLICATIONS

Yoshiko Seo et al. Usage experiment of the latest mammography system-Usage of Scanning information input function (Exam-Marker), Innervision, Vo. 27, No. 1, 2012, pp. 76-79 ( with Partial English Translation).

(Continued)

*Primary Examiner* — Tahmina Ansari
(74) *Attorney, Agent, or Firm* — Oblon, McClelland, Maier & Neustadt, L.L.P.

(57) ABSTRACT

A medical image processing apparatus according to an embodiment includes a detection unit, a generating unit, and an associating unit. The detection unit analyzes a first piece and a second piece of image data of a breast, and detects the positions of a chest wall and a nipple in each of the pieces of image data, wherein the first piece of image data is three-dimensional medical image data and the second piece of image data is medical image data of a different type from the first piece of image data. The generating unit generates a first sectional image and a second sectional image based on the first piece and second piece of image data, respectively. The associating unit associates the positional relation of the breast in the pieces of image data so that the positions of the chest wall and the nipple match between the pieces of image data.

17 Claims, 19 Drawing Sheets

(51) Int. Cl.
*A61B 8/08* (2006.01)
*A61B 10/00* (2006.01)
*A61B 5/00* (2006.01)
*G06T 7/00* (2006.01)
*A61B 5/055* (2006.01)
*A61B 6/04* (2006.01)
*A61B 8/00* (2006.01)

(52) U.S. Cl.
CPC .......... *A61B 6/5247* (2013.01); *A61B 8/4416* (2013.01); *A61B 8/5261* (2013.01); *A61B 10/0041* (2013.01); *G06T 7/0028* (2013.01); *G06T 7/0038* (2013.01); *A61B 5/055* (2013.01); *A61B 6/0414* (2013.01); *A61B 8/0825* (2013.01); *A61B 8/403* (2013.01); *A61B 8/483* (2013.01); *A61B 2576/02* (2013.01); *G06T 2207/10081* (2013.01); *G06T 2207/10136* (2013.01); *G06T 2207/30068* (2013.01)

(56) References Cited

U.S. PATENT DOCUMENTS

| 8,496,586 B2* | 7/2013 | Zhang | A61B 6/463 |
| | | | 600/407 |
| 2010/0280375 A1* | 11/2010 | Zhang | A61B 6/463 |
| | | | 600/443 |
| 2015/0221091 A1* | 8/2015 | Sugiyama | A61B 6/502 |
| | | | 382/131 |

OTHER PUBLICATIONS

J-Start Comparison test for verifying the efficiency of breast cancer screening using ultrasonography, http://www.j-start.org/, 2013, 3 pages (with Partial English translation).

* cited by examiner

MEDICAL IMAGE PROCESSING APPARATUS AND MEDICAL IMAGE DIAGNOSTIC APPARATUS FOR ASSOCIATING A POSITIONAL RELATION OF A BREAST BETWEEN PIECES OF IMAGE DATA

CROSS-REFERENCE TO RELATED APPLICATIONS

This application is based upon and claims the benefit of priority from Japanese Patent Application No. 2014-019761, filed on Feb. 4, 2014; the entire contents of which are incorporated herein by reference.

FIELD

Embodiments described herein relate to a medical image processing apparatus, a medical image diagnostic apparatus, and a method for processing a medical image.

BACKGROUND

Mammary gland image diagnosis performed in examinations for breast cancer or the like has been generally performed using mammography images imaged by mammography apparatuses. Meanwhile, a project called Japan Strategic Anti-cancer Randomized Trial (J-START) has been recently started, and in examinations for breast cancer, mammary gland image diagnosis that uses both the mammography image and the ultrasonic image in combination has been started to be performed.

Ultrasonic diagnostic apparatuses and mammography apparatuses that can perform the imaging of three-dimensional image data (called volume data) have been recently used in examination of breasts. For example, as such an ultrasonic diagnostic apparatus, automated whole breast imaging ultrasonic apparatuses such as an automated breast ultrasound system (ABUS) and an automated breast volume sonography (ABVS) are known. For example, as such a mammography apparatus, computed tomography (CT) specialized in tomosynthesis and breast imaging is known.

DETAILED DESCRIPTION

The following describes embodiments of a medical image processing apparatus, a medical image diagnostic apparatus, and a method for processing a medical image with reference to the drawings.

First Embodiment

A medical image diagnostic apparatus according to the first embodiment includes a detection unit, a generating unit, an associating unit, and a display. The detection unit analyzes a first piece of image data obtained by imaging a breast of a subject and a second piece of image data obtained by imaging the breast, and detects the positions of a chest wall and a nipple in each of the pieces of image data, wherein the first piece of image data is three-dimensional medical image data and the second piece of image data is medical image data of a different type from the first piece of image. The generating unit generates a first sectional image based on the first piece of image data and generates a second sectional image based on the second piece of image data. The associating unit associates the positional relation of the breast in the first piece of image data and the second piece of image data so that the positions of the chest wall and the nipple match between the first and the second pieces of image data. The display displays the first sectional image, the second sectional image, and a mark indicating the positional relation of the breast.

The first embodiment describes an example of a case in which the medical image diagnostic apparatus is an ultrasonic diagnostic apparatus. The first embodiment describes an example of a case in which the first piece of image data is three-dimensional ultrasonic images, whereas the second piece of image data is three-dimensional mammography image data.

Figure 1:
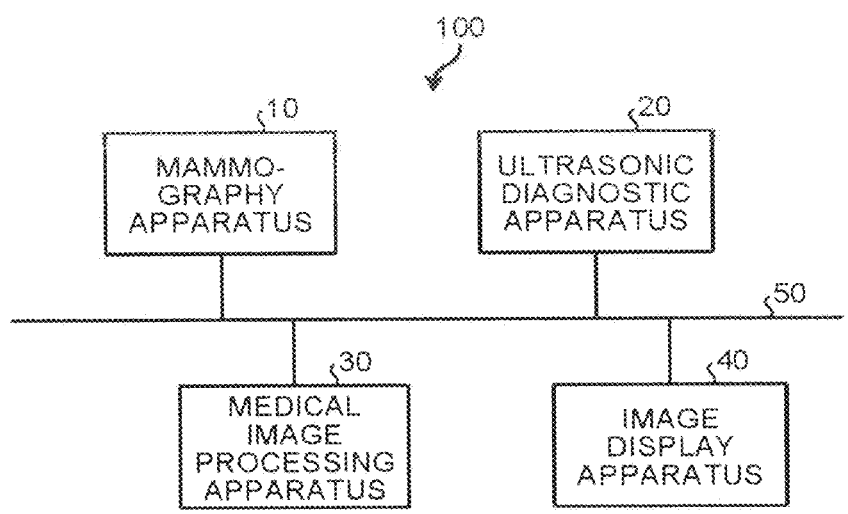
FIG. 1 is a diagram illustrating a configuration example of a medical image processing system according to a first embodiment.

FIG. 1 is a diagram illustrating a configuration example of a medical image processing system according to the first embodiment. The medical image processing system according to the present embodiment is installed in hospitals that perform examinations for breast cancer and is used for mammary gland diagnosis that uses both a mammography image and an ultrasonic image in combination.

As illustrated in FIG. 1, for example, this medical image processing system 100 according to the present embodiment includes a mammography apparatus 10, an ultrasonic diagnostic apparatus 20, a medical image processing apparatus 30, and an image display apparatus 40. The apparatuses are connected via a network 50 and mutually transmit and receive images imaged by the mammography apparatus 10 and the ultrasonic diagnostic apparatus 20 or the like.

The mammography apparatus 10 irradiates a breast of a subject with X-rays and detects X-rays passed through the breast to generate mammography image data. For example, the mammography apparatus 10 generates three-dimensional mammography image data obtained by imaging the breast of the subject.

The ultrasonic diagnostic apparatus 20 generates ultrasonic image data based on reflected wave data collected by scanning the subject with an ultrasonic probe that transmits and receives ultrasonic waves. For example, the ultrasonic diagnostic apparatus 20 generates three-dimensional ultrasonic image data obtained by imaging the breast of the subject.

The medical image processing apparatus 30 acquires the mammography image data from the mammography apparatus 10 via the network 50 and acquires the ultrasonic image data from the ultrasonic diagnostic apparatus 20. The medical image processing apparatus 30 performs various kinds of image processing using the acquired mammography image data and ultrasonic image data and displays various kinds of images generated by the image processing. The medical image processing apparatus 30 is, for example, an image storage server or a workstation.

The image display apparatus 40 acquires the various images from the medical image processing apparatus 30 via the network 50 and displays them. The image display apparatus 40, which is, for example, a tablet terminal portable by an operator, is connected to the network 50 via a wireless local area network (LAN). The image display apparatus 40 may be a notebook computer or a desktop PC or may be connected to the network 50 via a wired LAN.

Mammary gland image diagnosis performed in examinations for breast cancer or the like has been generally performed using mammography images imaged by mammography apparatuses. Meanwhile, a project called Japan Strategic Anti-cancer Randomized Trial (J-START) has been recently started, and in examinations for breast cancer, mammary gland image diagnosis that uses both the mammography image and the ultrasonic image in combination has been started to be performed.

In the mammary gland image diagnosis that uses both the mammography image and the ultrasonic image in combination, first, a mammography image of a breast of a subject is imaged using a mammography apparatus. Thereafter, on the same day or another day, an ultrasonic image of the same subject is imaged by an ultrasonic diagnostic apparatus while referring to the mammography image and its findings. In such mammary gland image diagnosis, a technician who images and interprets the mammography image is generally different from a technician who images and interprets the ultrasonic image in many cases. For that reason, in order to perform ultrasonography while referring to the mammography image and its findings, sufficient knowledge and understanding about the interpretation of and findings about the mammography image have been required for technicians taking charge of ultrasonography.

Ultrasonic diagnostic apparatuses and mammography apparatuses that can perform the imaging of three-dimensional image data (called volume data) have been recently used in the examination of breasts. For example, as such an ultrasonic diagnostic apparatus, automated whole breast imaging ultrasonic apparatuses such as an automated breast ultrasound system (ABUS) and an automated breast volume sonography (ABVS) are known. For example, as such a mammography apparatus, computed tomography (CT) specialized in tomosynthesis and breast imaging are known. When the mammary gland image diagnosis is performed by using both three-dimensional mammography image data and three-dimensional ultrasonic image data in combination, a load related to interpretation is considered to further increase, because three-dimensional image data generally has a large amount of data.

In view of the above circumstances, in the present embodiment, the ultrasonic diagnostic apparatus 20 displays a first sectional image generated based on the three-dimensional ultrasonic image data and a second sectional image generated based on the three-dimensional mammography image data together with information indicating the positional relation of a breast drawn in the respective sectional images. This display facilitates technicians of ultrasonography to compare the ultrasonic image and the mammography image, thereby reducing the load related to interpretation in the mammary gland image diagnosis using both the three-dimensional mammography image data and three-dimensional ultrasonic image data in combination.

The following describes functions of the respective apparatuses of the medical image processing system 100 according to the present embodiment in detail.

Figure 2:
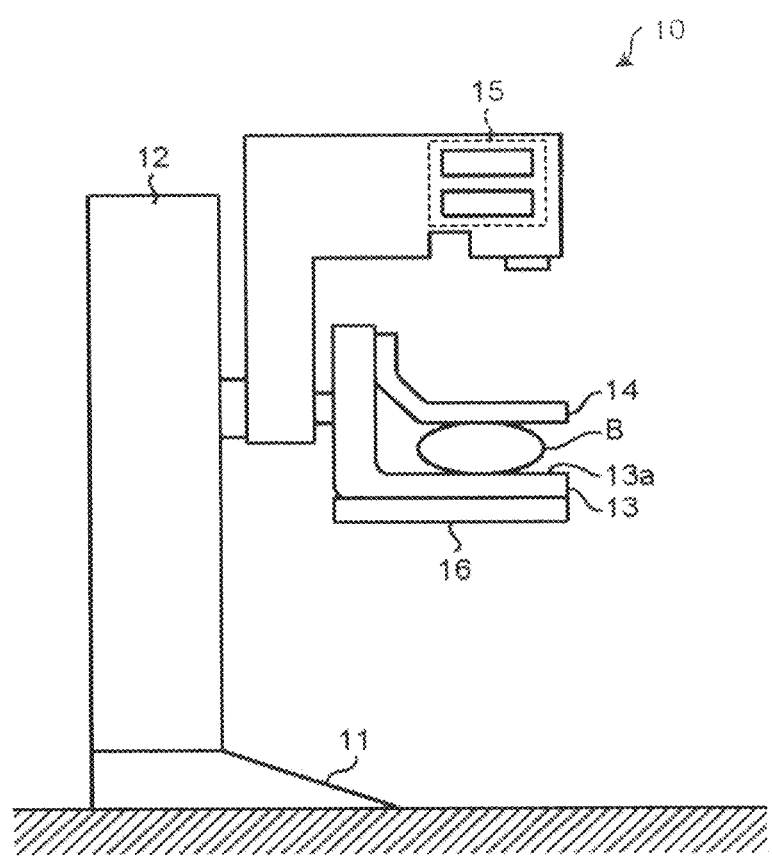
FIGS. 2 and 3 are diagrams illustrating a configuration example of a mammography apparatus according to the first embodiment.
Figure 3:
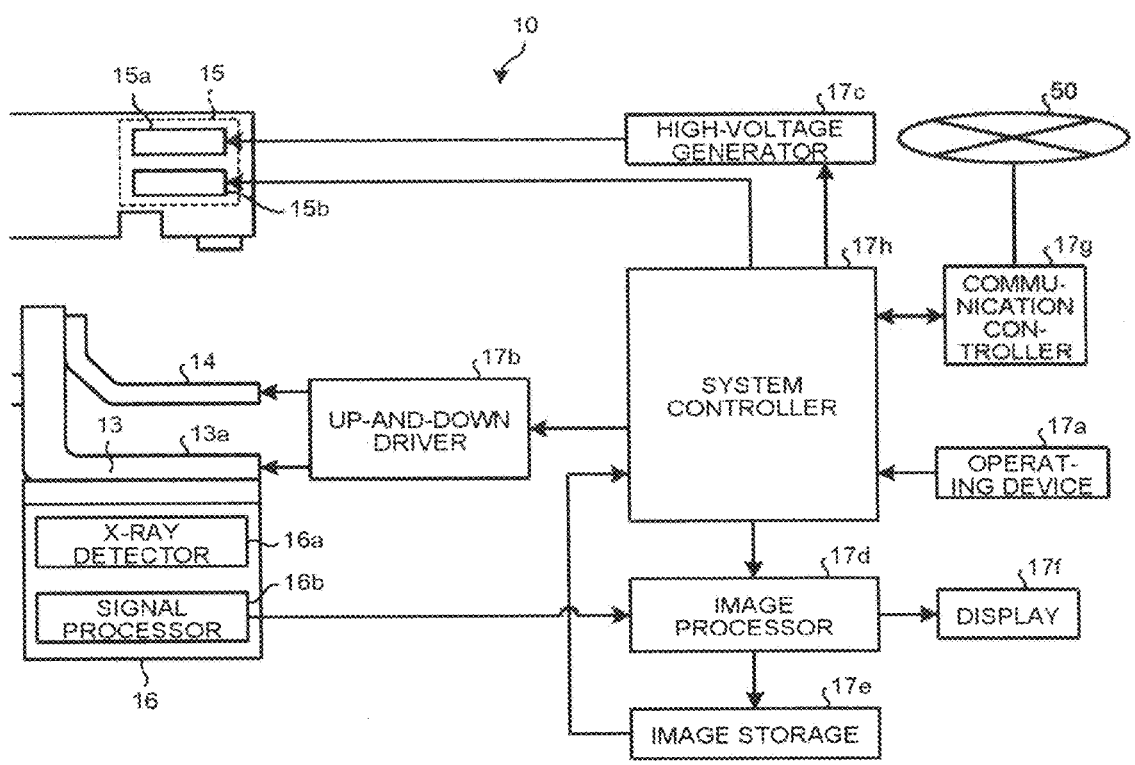

FIGS. 2 and 3 are diagrams illustrating a configuration example of the mammography apparatus 10 according to the first embodiment. As illustrated in FIG. 2, for example, the mammography apparatus 10 includes a base 11 and a stand 12. The stand 12 is erected on the base 11 to support an imaging stage 13, a pressurizing plate 14, an X-ray output device 15, and an X-ray detector 16. The imaging stage 13, the pressurizing plate 14, and the X-ray detector 16 are supported movably in the up-and-down direction.

The imaging stage 13 is a stage to support a breast B of a subject and has a support face 13a on which the breast B is mounted. The pressurizing plate 14 is arranged above the imaging stage 13 and is arranged facing the imaging stage 13 in parallel and movable in a direction approaching and separating from the imaging stage 13. The pressurizing plate 14 pressurizes the breast B supported on the imaging stage 13 when moved in a direction approaching the imaging stage 13. The breast B pressurized by the pressurizing plate 14 is thinly spread out, which reduces overlapping of mammary glands within the breast B.

As illustrated in FIG. 3, the mammography apparatus 10 includes an operating device 17a, an up-and-down driver 17b, a high-voltage generator 17c, an image processor 17d, an image storage 17e, a display 17f, a communication controller 17g, and a system controller 17h. The operating device 17a accepts operation of inputting various kinds of commands from the operator. The up-and-down driver 17b is connected to the imaging stage 13 and moves up and down the imaging stage 13 in an up-and-down direction. The up-and-down driver 17b is connected to the pressurizing plate 14 and moves up and down the pressurizing plate 14 in the up-and-down direction (the direction approaching and separating from the imaging stage 13).

The X-ray output device 15 includes an X-ray tube 15a and an X-ray aperture 15b. The X-ray tube 15a generates X-rays. The X-ray aperture 15b is arranged between the X-ray tube 15a and the pressurizing plate 14 and controls the irradiation range of the X-rays generated from the X-ray tube 15a. The high-voltage generator 17c is connected to the X-ray tube 15a and supplies high voltage for the X-ray tube 15a to generate the X-rays.

The X-ray detector 16 includes an X-ray detector 16a and a signal processor 16b. The X-ray detector 16a detects X-rays passed through the breast B and the imaging stage 13 and converts them into electric signals (transmitted X-ray data). The signal processor 16b generates X-ray projection data from the electric signals converted by the X-ray detector 16a.

The image processor 17d is connected to the signal processor 16b and the image storage 17e, generates mammography image data based on the X-ray projection data generated by the signal processor 16b, and stores the generated mammography image data in the image storage 17e. The image processor 17d is connected to the display 17f and generates various kinds of images based on the generated mammography image data to display them on the display 17f. The image processor 17d can switch the kinds of the mammography data to be generated based on input operation from the operating device 17a.

In the present embodiment, the image processor 17d generates three-dimensional mammography image data obtained by imaging the breast B of the subject. For example, the image processor 17d generates the three-dimensional mammography image data based on X-ray projection data obtained by irradiating the breast B of the subject with X-rays from a plurality of different directions by moving the X-ray output device 15. In the following, the three-dimensional mammography image data generated by the image processor 17d will be called second volume data.

The communication controller 17g controls communication performed with the other apparatuses via the network 50. For example, the communication controller 17g transfers the mammography image data generated by the image processor 17d to the other apparatuses via the network 50. The mammography image data transferred via the network 50 can be subjected to image display, image processing, or the like in an apparatus as a transfer destination.

The system controller 17h is connected to the operating device 17a, the up-and-down driver 17b, the high-voltage generator 17c, the X-ray aperture 15b, the image processor 17d, the image storage 17e, and the communication controller 17g and collectively controls the entire mammography apparatus 10.

Figure 4:
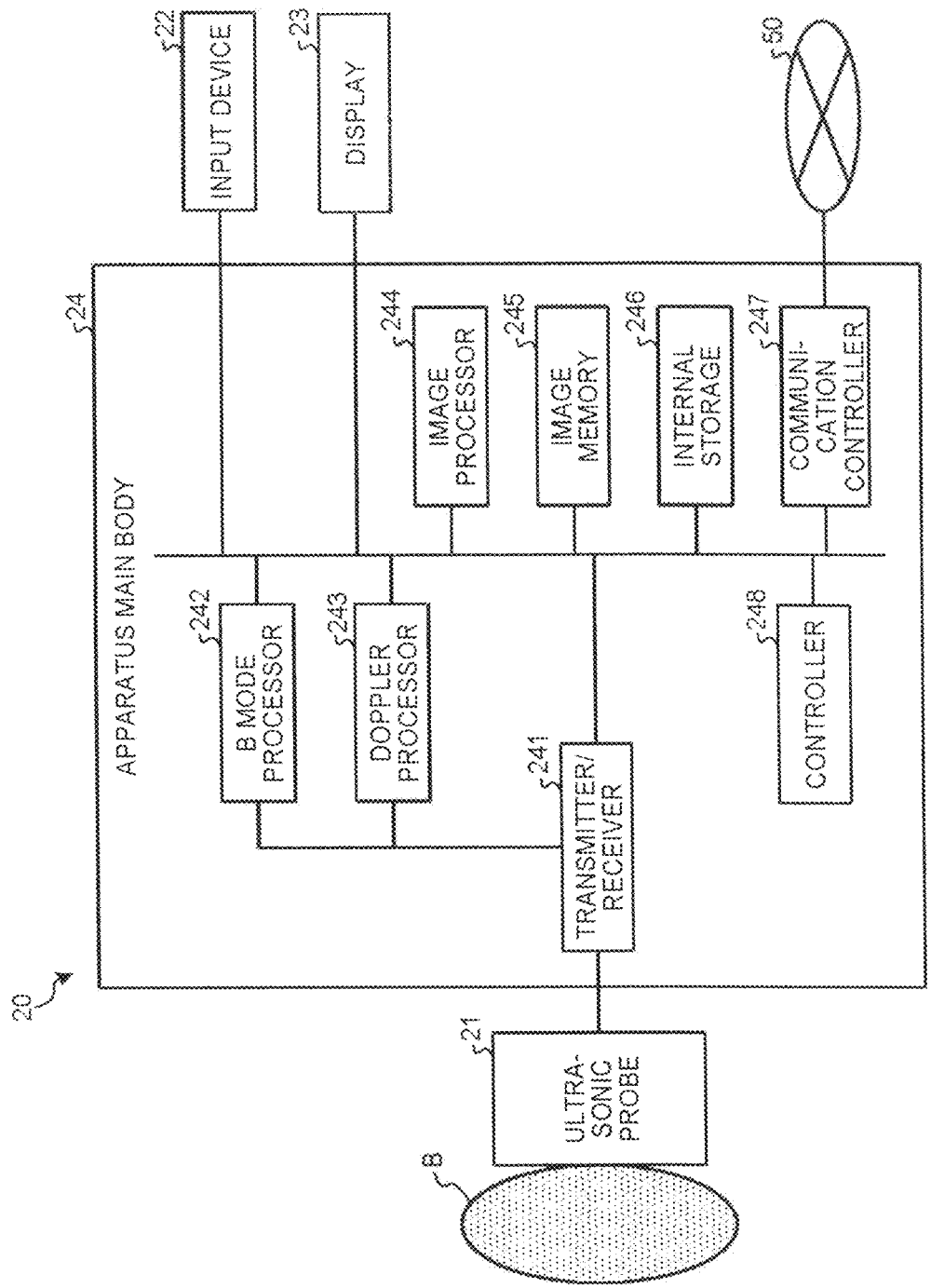
FIG. 4 is a diagram illustrating a configuration example of an ultrasonic diagnostic apparatus according to the first embodiment.

FIG. 4 is a diagram illustrating a configuration example of the ultrasonic diagnostic apparatus 20 according to the first embodiment. As illustrated in FIG. 4, the ultrasonic diagnostic apparatus 20 according to the present embodiment includes an ultrasonic probe 21, a display 23, an input device 22, and an apparatus main body 24.

The ultrasonic probe 21 includes a plurality of piezoelectric transducer elements. The piezoelectric transducer elements generate ultrasonic pulses based on drive signals supplied from a transmitter/receiver 241 of the apparatus main body 24 described below, receive reflected waves from the breast B of the subject, and convert them into electric signals. The ultrasonic probe 21 includes a matching layer provided in a piezoelectric transducer element and a backing member that prevents ultrasonic waves from being transmitted backward from the piezoelectric transducer element.

In the present embodiment, the ultrasonic probe 21 is a probe that can collect volume data as three-dimensional image data. For example, the ultrasonic probe 21 is a 2D array probe or a mechanical 4D probe.

When the ultrasonic probe 21 transmits the ultrasonic pulses to the breast B of the subject, the transmitted ultrasonic pulses are successively reflected by discontinuous surfaces in acoustic impedance in the body tissues of the breast B and are received as echo signals by the piezoelectric transducer elements of the ultrasonic probe 21. The amplitude of the received echo signals depends on a difference in acoustic impedance on the discontinuous surface by which the ultrasonic pulse is reflected. The echo signal when the transmitted ultrasonic pulse is reflected by a moving bloodstream or surface such as a heart wall is subjected to frequency shift depending on the velocity component of a moving body with respect to the ultrasonic transmission direction by the Doppler effect.

The display 23 is a monitor or the like and displays a graphical user interface (GUI) for an operator of the ultrasonic diagnostic apparatus 20 to input various kinds of instructions and setting requests using the input device 22 and ultrasonic images and analysis results generated by the apparatus main body 24.

The input device 22 is a mouse, a keyboard, a button, a panel switch, a touch command screen, a foot switch, a track ball, or the like and is connected to the apparatus main body 24. The input device 22 accepts the various kinds of instructions and setting requests from the operator of the ultrasonic diagnostic apparatus 20 and transfers the accepted various kinds of instructions and setting requests to the apparatus main body 24.

The apparatus main body 24 generates ultrasonic image data based on the reflected waves received by the ultrasonic probe 21. As illustrated in FIG. 4, the apparatus main body 24 includes a transmitter/receiver 241, a B mode processor 242, a Doppler processor 243, an image processor 244, an image memory 245, a controller 248, an internal storage 246, a communication controller 247, and a controller 248.

The transmitter/receiver 241 includes a trigger generating circuit, a transmission delay circuit, and a pulser circuit and supplies drive signals to the ultrasonic probe 21. The pulser circuit repeatedly generates rate pulses for forming an ultrasonic pulse at a given pulse repetition frequency (PRF). PRF is also called a rate frequency. The transmission delay circuit gives transmission delay times for the respective piezoelectric transducer elements required for focusing the ultrasonic pulse generated by the ultrasonic probe 21 into a beam form and determining transmission directivity to the respective rate pulses generated by the pulser circuit. The trigger generating circuit applies drive signals (drive pulses)

to the ultrasonic probe 21 with timing based on the rate pulses. In other words, the transmission delay circuit changes the transmission delay times to be given to the respective rate pulses, thereby freely adjusting a transmission direction from a piezoelectric transducer element face.

The transmitter/receiver 241 has a function that can instantly change a transmission frequency, a transmission drive voltage, or the like in order to perform a given scan sequence based on instructions by the controller 248 described below. In particular, changes of the transmission drive voltage can be performed by a linear amplifier type oscillator circuit that can instantly switch the values or a mechanism that electrically switch a plurality of power supply units.

The transmitter/receiver 241 includes an amplifier circuit, an analog/digital (A/D) converter, a reception delay circuit, an adder, and a quadrature detection circuit and performs various kinds of processing on reflected wave signals received by the ultrasonic probe 21 to generate reflected wave data. The amplifier circuit amplifies the reflected wave signals for each channel to perform gain correction processing. The A/D converter performs A/D conversion on the reflected wave signals subjected to the gain correction. The reception delay circuit gives reception delay times necessary for determining reception directivity for digital data. The adder performs addition processing on the reflected wave signals with the reception delay times given by the reception delay circuit. The addition processing by the adder enhances a reflected component from a direction responsive to the reception directivity of the reflected wave signals. The quadrature detection circuit converts an output signal of the adder into an in-phase signal (I signal, I: In-phase) and a quadrature signal (Q signal, Q: Quadrature-phase) in a baseband and stores the converted I signal and Q signal (hereinafter, denoted as an IQ signal) as a reception signal (reflected wave data) in a frame buffer (not illustrated). The quadrature detection circuit may convert the output signal of the adder into a radio frequency (RF) signal and store it in the frame buffer (not illustrated). The IQ signal and the RF signal are reception signals having phase information.

The B mode processor 242 receives the reflected wave data from the transmitter/receiver 241 and performs logarithmic amplification, envelope detection processing, or the like to generate data (B mode data), in which signal intensity is represented by brightness. The B mode processor 242 generates M mode data described below.

The Doppler processor 243 performs frequency analysis on velocity information from the reflected wave data received from the transmitter/receiver 241, extracts blood stream, tissue, and contrast medium echo components by the Doppler effect, and generates data (Doppler data) that extracts moving body information such as average speed, dispersion, and power for many points.

The image processor 244 generates ultrasonic images from the B mode data and the M mode data generated by the B mode processor 242 and the Doppler data generated by the Doppler processor 243. Specifically, the image processor 244 generates a B mode image from the B mode data, generates an M mode image from the M mode data, and generates a Doppler image from the Doppler data. The image processor 244 converts (scan converts) a scanning line signal stream of ultrasonic scanning into a scanning line signal stream of a video format represented by television by performing coordinate transformation or data interpolation and generates ultrasonic images (the B mode image, the M mode image, and the Doppler image) as display images.

In the present embodiment, the image processor 244 generates three-dimensional ultrasonic image data obtained by imaging the breast B of the subject. For example, the image processor 244 generates the three-dimensional ultrasonic image data from the B mode data generated by the B mode processor 242. Specifically, the image processor 244 performs coordination transformation or data interpolation on the B mode data generated by the B mode processor 242, thereby generating the three-dimensional ultrasonic image data. In the following, the three-dimensional ultrasonic image data generated by the image processor 244 will be called first volume data.

The image memory 245 is a memory that stores therein the ultrasonic image data generated by the image processor 244 and the images generated by performing image processing on the ultrasonic image data. For example, after diagnosis, the operator can retrieve images recorded during an examination and can reproduce the images in a still image manner or in a moving image manner by using a plurality of the images. The image memory 245 may store therein image brightness signals passed through the transmitter/receiver 241, other raw data, and image data acquired via the network 50.

The internal storage 246 stores therein apparatus control programs for performing ultrasonic transmission and reception, image processing, and display processing, diagnostic information (patients' IDs, doctors' opinions, for example), and various kinds of data such as diagnostic protocols and various kinds of setting information. The internal storage 246 may be used for the storage of the images stored in the image memory 245.

The communication controller 247 controls communication performed with the other apparatuses via the network 50. For example, the communication controller 247 transfers the ultrasonic image data generated by the image processor 244 to the other apparatuses via the network 50. The ultrasonic image data transferred via the network 50 can be subjected to image display, image processing, or the like in an apparatus as a transfer destination. The communication controller 247 receives various kinds of data generated by the other apparatuses via the network 50.

The controller 248 controls the entire processing in the ultrasonic diagnostic apparatus 20. Specifically, the controller 248 controls the processing of the transmitter/receiver 241, the B mode processor 242, the Doppler processor 243, and the image processor 244 based on the various kinds of instructions and setting requests input from the operator via the input device 22 and the various kinds of programs and various kinds of setting information read from the internal storage 246 and controls to display the ultrasonic images stored in the image memory 245 or the like on the display 23.

Figure 5:
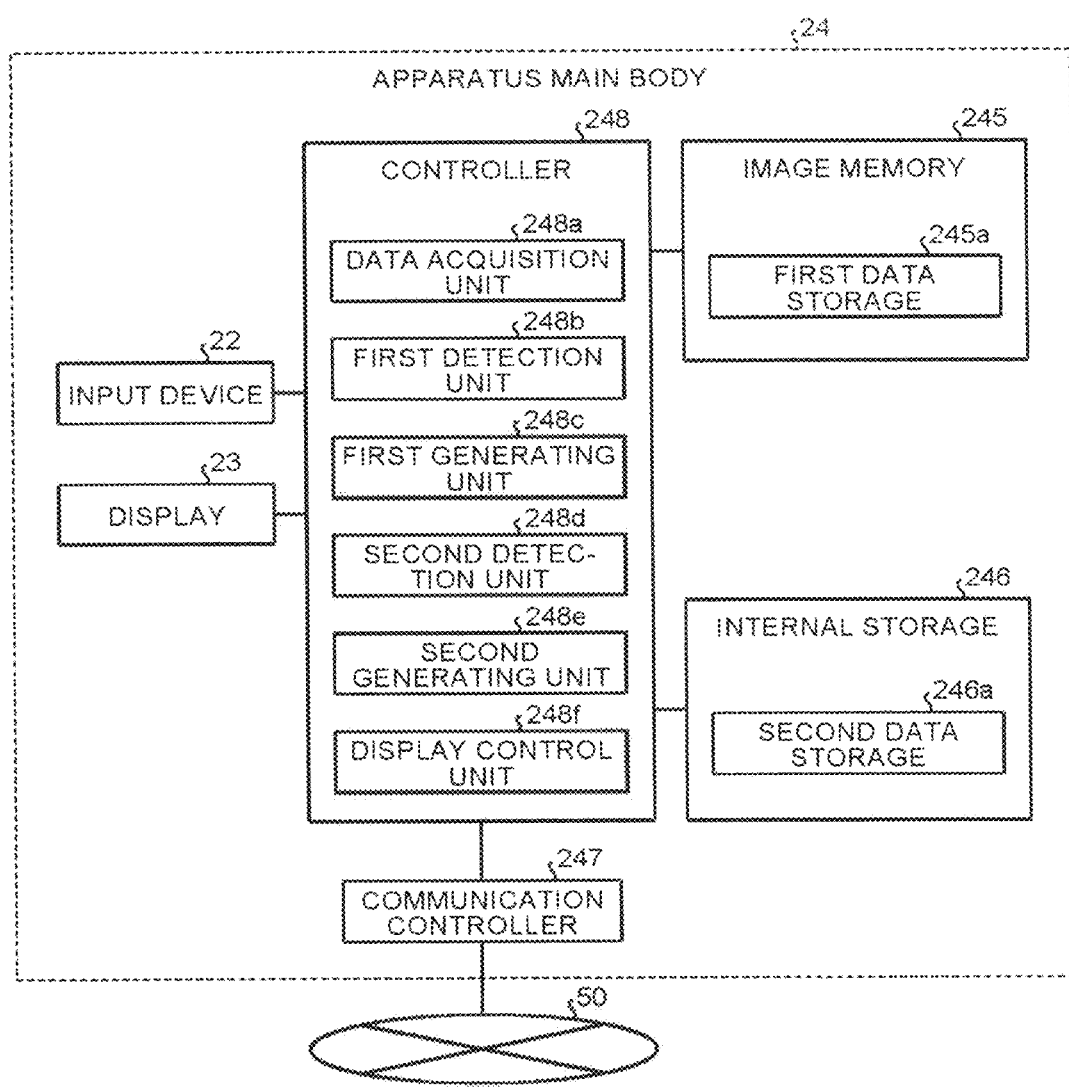
FIG. 5 is a diagram illustrating a detailed configuration example of the ultrasonic diagnostic apparatus according to the first embodiment.

FIG. 5 is a diagram illustrating a detailed configuration example of the ultrasonic diagnostic apparatus 20 according to the first embodiment. FIG. 5 illustrates, out of the configuration illustrated in FIG. 4, the input device 22, the display 23, the apparatus main body 24, the image memory 245, the internal storage 246, the communication controller 247, and the controller 248. The ultrasonic diagnostic apparatus 20 according to the first embodiment includes a first detection unit and a second detection unit as the above detection unit, includes a first generating unit and a second generating unit as the above generating unit, and includes a display control unit as the above associating unit.

As illustrated in FIG. 5, for example, the image memory 245 includes a first data storage 245a. The internal storage 246 includes a second data storage 246a. The first data storage 245a may be included in the internal storage 246. The second data storage 246a may be included in the image memory 245.

The first data storage 245a stores therein the first volume data as the three-dimensional ultrasonic image data obtained by imaging the breast B of the subject. The first volume data is, after starting imaging by the ultrasonic diagnostic apparatus 20, generated by the image processor 244 and is stored in the first data storage 245a.

The second data storage 246a stores therein the second volume data as the three-dimensional mammography image data obtained by imaging the breast B of the subject. The second volume data is acquired by a data acquisition unit 248a described below and is stored in the second data storage 246a.

As illustrated in FIG. 5, for example, the controller 248 includes the data acquisition unit 248a, a first detection unit 248b, a first generating unit 248c, a second detection unit 248d, a second generating unit 248e, and a display control unit 248f.

The data acquisition unit 248a acquires the second volume data as the three-dimensional mammography image data obtained by imaging the breast B of the subject. Specifically, the data acquisition unit 248a acquires the second volume data from the mammography apparatus 10 via the communication controller 247 and stores it in the second data storage 246a.

The data acquisition unit 248a may passively acquire the second volume data transmitted from the mammography apparatus 10 or may actively acquire the second volume data by transmitting a data acquisition request to the mammography apparatus 10. The data acquisition unit 248a may acquire the second volume data from the medical image processing apparatus 30 after the second volume data has been transmitted from the mammography apparatus 10 to the medical image processing apparatus 30.

Based on the first volume data as the three-dimensional ultrasonic image data obtained by imaging the breast B of the subject, the first detection unit 248b detects the positions of a chest wall and a nipple in the first volume data. Specifically, the first detection unit 248b reads the first volume data on the subject to be diagnosed from the first data storage 245a and detects the positions of the chest wall and the nipple based on the first volume data.

Figure 6:
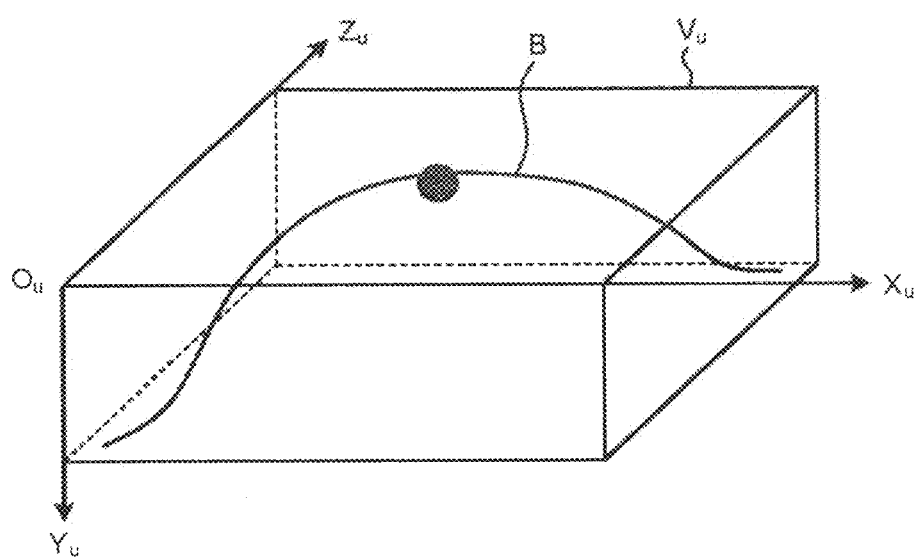
FIG. 6 is a diagram illustrating an example of first volume data according to the first embodiment.

FIG. 6 is a diagram illustrating an example of the first volume data according to the first embodiment. As illustrated in FIG. 6, for example, the first volume data $V_u$ is three-dimensional ultrasonic image data obtained by imaging the breast B of the subject and is represented by a three-dimensional coordinate system having an $X_u$ axis, a $Y_u$ axis, and a $Z_u$ axis that are orthogonal to each other on an origin $O_u$. For example, the $X_u$ axis is an axis in the scanning direction of the ultrasonic probe 21, the $Y_u$ axis is an axis in the depth direction of the subject (a direction from the body surface toward the thoracic cavity), and the $Z_u$ axis is an axis in a slicing direction.

For example, the first detection unit 248b detects the position of the chest wall by threshold processing based on the distribution of brightness vales of respective voxels contained in the first volume data.

Figure 7:
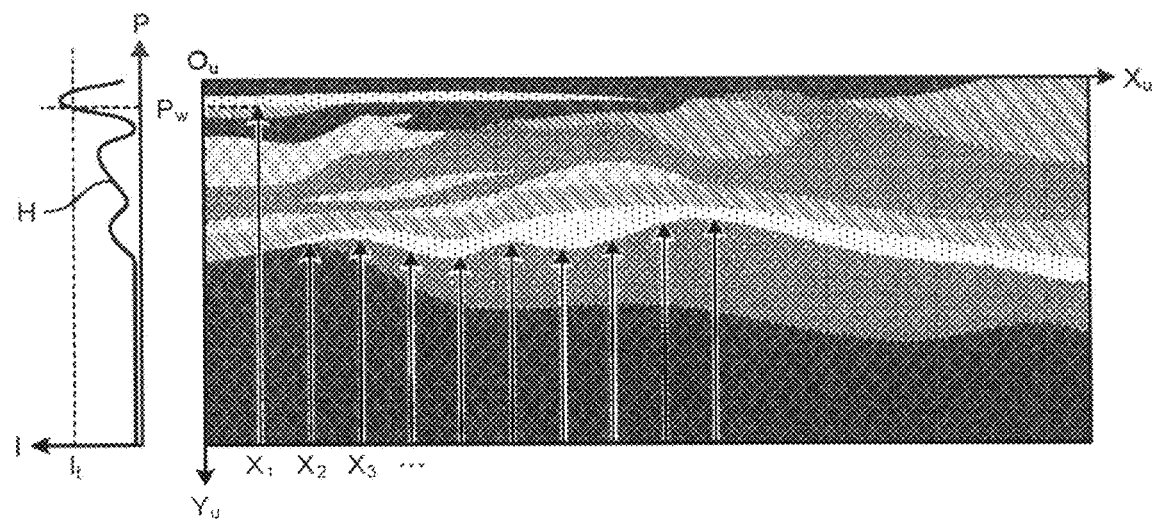
FIGS. 7 and 8 are diagrams illustrating an example of the position detection of a chest wall by a first detection unit according to the first embodiment.
Figure 8:
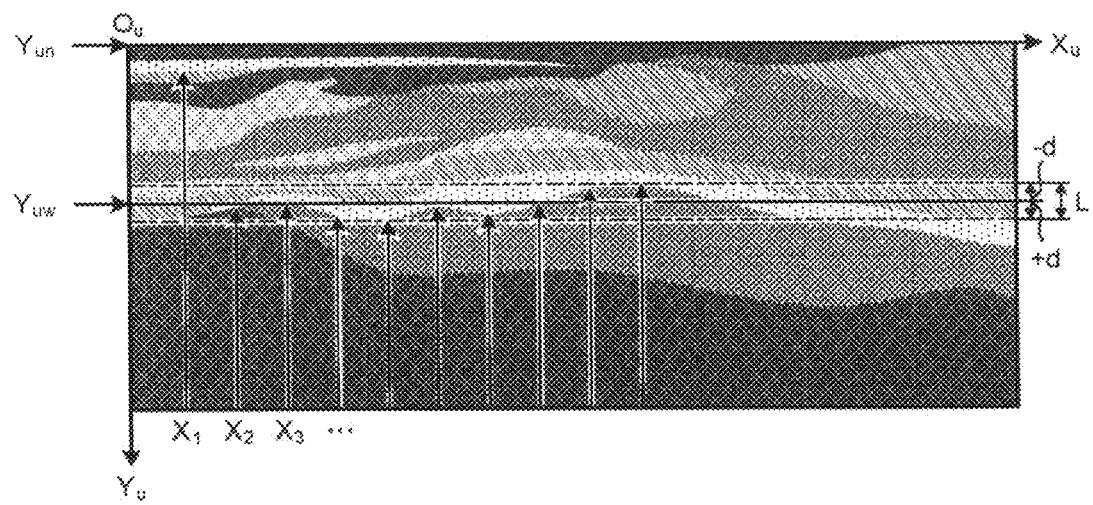

FIGS. 7 and 8 are diagrams illustrating an example of the position detection of the chest wall by the first detection unit 248b according to the first embodiment. FIGS. 7 and 8 illustrate one image among a plurality of sectional images in the scanning direction contained in the first volume data as an example. As illustrated in FIG. 7, for example, the first detection unit 248b sets examination points $X_1$, $X_2$, $X_3$, . . . at regular intervals along the side on the thoracic cavity side in each of the sectional images in the scanning direction.

The first detection unit 248b generates a histogram (a brightness value profile) H having a pixel value I in a direction P from the thoracic cavity side (the lower side illustrated in FIG. 7) toward the body surface side (the upper side illustrated in FIG. 7) for each of the set examination points. The first detection unit 248b then examines the pixel value I in order from the thoracic cavity side toward the body surface side for the respective generated histograms and extracts a position $P_w$ (the positions of the tips of the arrows extending from the respective examination points $X_1$, $X_2$, $X_3$, . . . illustrated in FIG. 7) of a pixel whose pixel value I has first exceeded a threshold $I_t$.

After that, as illustrated in FIG. 8, for example, the first detection unit 248b sets a range L having thicknesses +d and −d in the depth direction with any coronal image parallel to the $Z_u$-$X_u$ plane as a reference for the first volume data. The first detection unit 248b identifies the position of the range L containing the largest number of a plurality of positions $P_w$ extracted from the respective histograms within the first volume data and detects a position in the depth direction of the coronal image as the reference in the identified range L as a position $Y_{uw}$ of the chest wall in the first volume data.

For example, the first detection unit 248b detects the position of a coronal image closest to the body surface in the first volume data as the position of the nipple. In the imaging by the ultrasonic diagnostic apparatus 20, the ultrasonic probe 21 is brought into contact with the body surface of the subject to perform imaging. Because of this, the position of the coronal image closest to the body surface can be regarded as the position of the nipple. Specifically, the first detection unit 248b detects the position of the coronal image closest to the body surface (the upper side in FIG. 8) among a plurality of coronal images that can be generated from the first volume data as a position $Y_{un}$ of the nipple.

Figure 9:
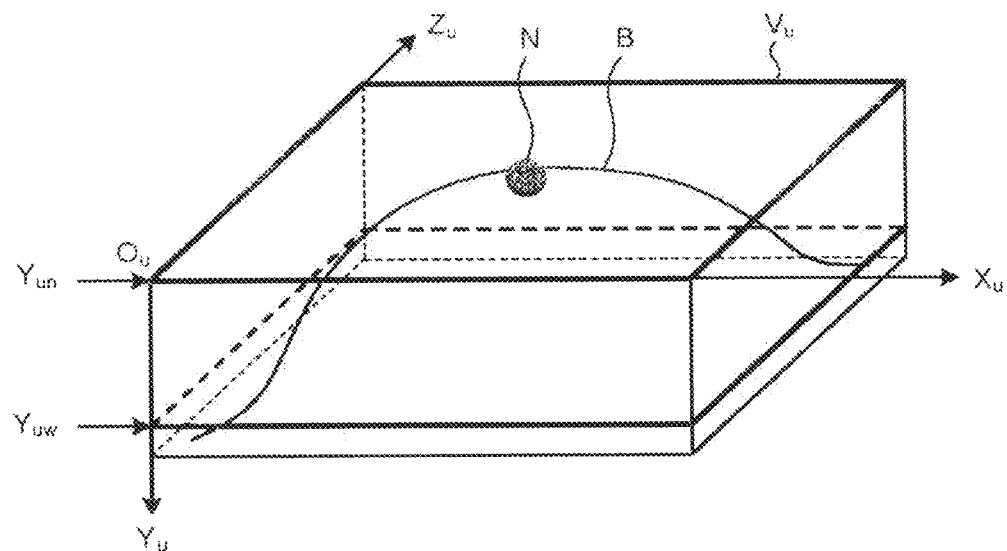
FIG. 9 is a diagram illustrating an example of a chest wall and a nipple detected by the first detection unit according to the first embodiment.

FIG. 9 is a diagram illustrating an example of the chest wall and the nipple detected by the first detection unit 248b according to the first embodiment. As illustrated in FIG. 9, for example, the first detection unit 248b detects the position $Y_{uw}$ of the chest wall and the position $Y_{un}$ of the nipple N in the depth direction (the $Y_u$ axial direction) based on the first volume data $V_u$ illustrated in FIG. 6. As described above, the position $Y_{uw}$ of the chest wall is detected as the position of the coronal image containing the chest wall, and the position $Y_{un}$ of the nipple N is detected as the position of the coronal image containing the nipple N.

Although described is an example of a case in which the first detection unit 248b detects the position of the chest wall by the threshold processing, that is not limiting; for example, the first detection unit 248b may detect the position of the chest wall using a certain method of edge detection.

For example, the first detection unit 248b may detect the position of the chest wall using a method of differential edge detection based on the distribution of the brightness values of the respective voxels contained in the first volume data. The method of differential edge detection is a method for detecting zero crossing of the second derivative of a gradient direction in the gradient of the brightness value against changes in the brightness value and can determine the position of an edge in an image with the accuracy of subpixel.

For example, the first detection unit 248b may detect the position of the chest wall using the Sobel operator based on the distribution of the brightness values of the respective voxels contained in the first volume data. The Sobel operator is a method that determines the intensity (differential value)

of the gradient of the brightness value by local product-sum operation against changes in the brightness value. For example, the Sobel operator uses the following coefficient matrices $f_x$ and $f_y$; $f_x$ is a coefficient matrix for detecting a longitudinal edge, whereas $f_y$ is a coefficient matrix for detecting a lateral edge.

$$f_x: \begin{pmatrix} -1 & 0 & 1 \\ -2 & 0 & 2 \\ -1 & 0 & 1 \end{pmatrix} \quad f_y: \begin{pmatrix} -1 & -2 & -1 \\ 0 & 0 & 0 \\ 1 & 2 & 1 \end{pmatrix}$$

The intensity $|\nabla f|$ of the gradient of the brightness value is determined by the following Expression (1):

$$|\nabla f| = \sqrt{f_x^2 + f_y^2} \quad (1)$$

The direction θ of the edge is determined by the following Expression (2):

$$\theta = \tan^{-1}(f_x/f_y) \quad (2)$$

In this case, for example, the first detection unit 248b detects the position of the edge using the method of differential edge detection or the Sobel operator for the respective histograms of the pixel value generated for each of the examination points $X_1, X_2, X_3, \ldots$ based on the volume data of the B mode image. The first detection unit 248b uses the detected position of the edge as the above position $P_w$, thereby detecting the position of the chest wall in the first volume data.

Although described is an example of a case in which the first detection unit 248b automatically detects the positions of the chest wall and the nipple, that is not limiting; for example, the first detection unit 248b may accept operation designating the positions of the chest wall and the nipple from the operator via the input device 22, thereby detecting the positions of the chest wall and the nipple in the first volume data.

In this case, for example, the first detection unit 248b generates a plurality of coronal images based on the first volume data and causes the display 23 to display the generated coronal images in order in accordance with operation by the operator. The first detection unit 248b accepts operation to select a coronal image to be the section of the chest wall from the displayed coronal images from the operator and detects the position of the section selected by the operation as the position $Y_{uw}$ of the chest wall. Similarly, the first detection unit 248b accepts operation to select a coronal image to be the section of the nipple from the operator and detects the position of the section selected by the operation as the position $Y_{un}$ of the nipple.

Returning back to FIG. 5, the first generating unit 248c generates the first sectional image based on the first volume data. Specifically, the first generating unit 248c reads the first volume data on the subject to be diagnosed from the first data storage 245a and generates the first sectional image based on the first volume data. For example, the first generating unit 248c generates the first sectional image by performing multi-planar reconstruction (MPR) using the first volume data.

Figure 10:
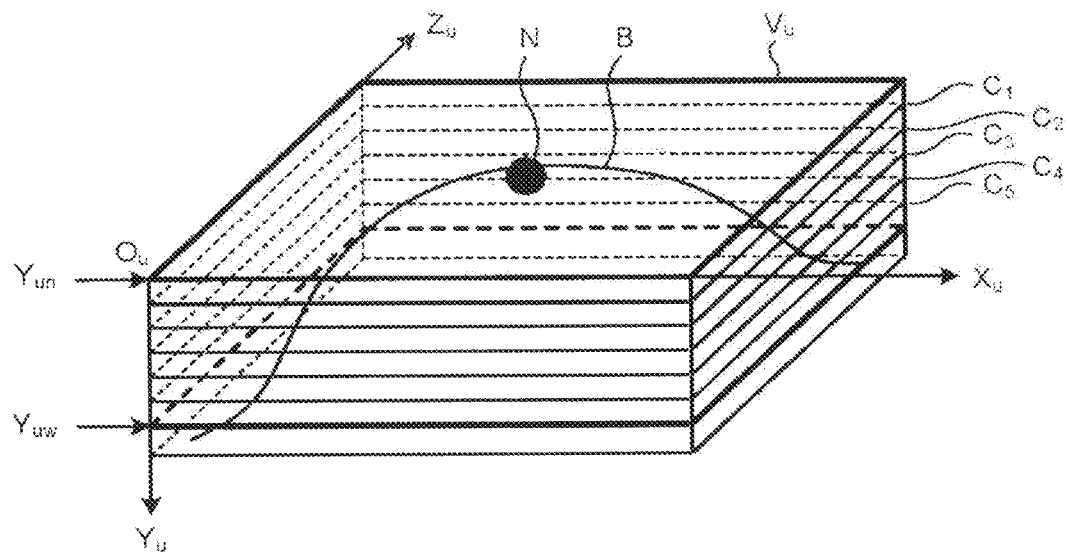
FIG. 10 is a diagram illustrating an example of the generation of a first sectional image by a first generating unit according to the first embodiment.

FIG. 10 is a diagram illustrating an example of the generation of the first sectional image by the first generating unit 248c according to the first embodiment. As illustrated in FIG. 10, for example, the first generating unit 248c generates as the first sectional image a plurality of coronal images $C_1$ to $C_5$ that divide the section between the position $Y_{uw}$ of the chest wall and the position $Y_{un}$ of the nipple N detected by the first detection unit 248b in the depth direction at regular intervals. In the present embodiment, the first generating unit 248c further generates an axial image and a sagittal image in which the breast B of the subject is drawn based on the first volume data.

Returning back to FIG. 5, based on the second volume data as the three-dimensional mammography image data obtained by imaging the breast B of the subject, the second detection unit 248d detects the positions of the chest wall and the nipple in the second volume data. Specifically, the second detection unit 248d reads the second volume data on the subject to be diagnosed from the second data storage 246a and detects the positions of the chest wall and the nipple based on the second volume data.

Figure 11:
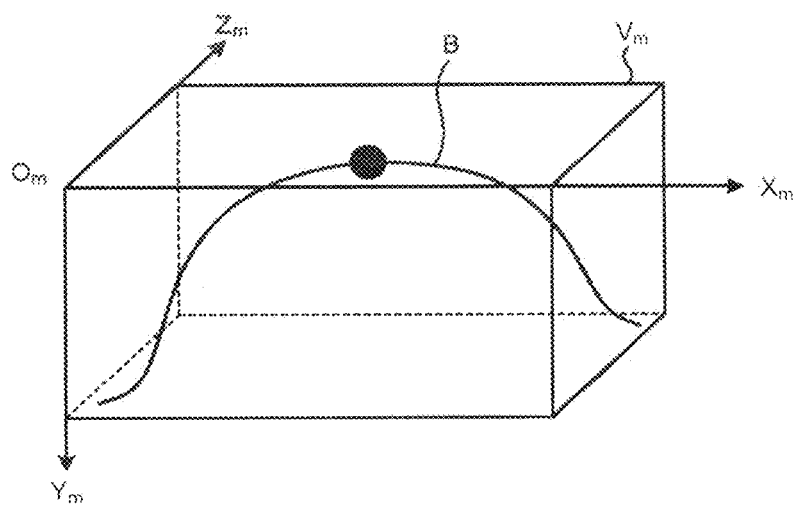
FIG. 11 is a diagram illustrating an example of second volume data according to the first embodiment.

FIG. 11 is a diagram illustrating an example of the second volume data according to the first embodiment. As illustrated in FIG. 11, for example, this second volume data $V_m$ is three-dimensional mammography image data obtained by imaging the breast B of the subject and is represented by a three-dimensional coordinate system having an $X_m$ axis, a $Y_m$ axis, and a $Z_m$ axis that are orthogonal to each other on an origin $O_m$. For example, the $X_m$ axis is an axis in the moving direction of the X-ray output device 15 when irradiating the subject with X-rays from a plurality of different directions, the $Y_m$ axis is an axis in the depth direction of the subject (a direction from the body surface toward the thoracic cavity), and the $Z_m$ axis is an axis in the direction from the pressurizing plate 14 toward the support face 13a of the imaging stage 13 in the mammography apparatus 10.

Figure 12:
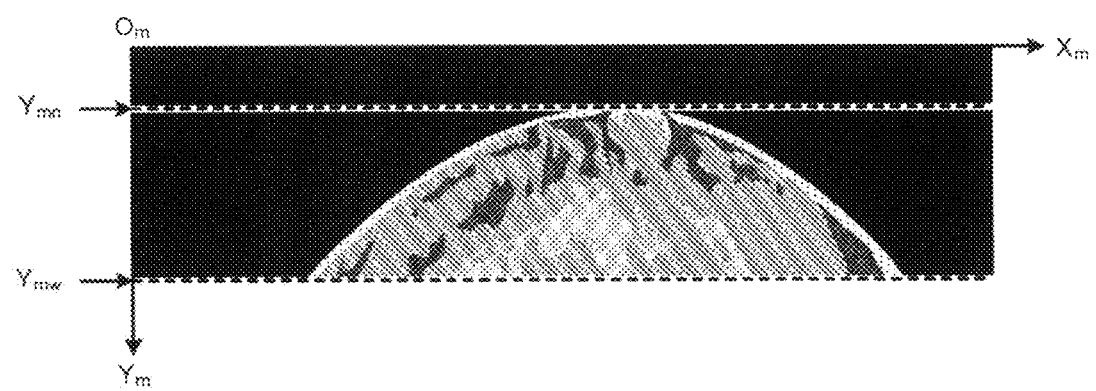
FIG. 12 is a diagram illustrating an example of the position detection of a chest wall by a second detection unit according to the first embodiment.

FIG. 12 is a diagram illustrating an example of the position detection of the chest wall and the nipple by the second detection unit 248d according to the first embodiment. FIG. 12 illustrates one image among a plurality of sectional images parallel to the pressurizing plate 14 and the imaging stage 13 contained in the second volume data as an example.

For example, the second detection unit 248d detects the position of a coronal image closest to the thoracic cavity in the second volume data as the position of the chest wall. General imaging by the mammography apparatus 10 has such a setting that the chest wall is positioned at an end of a mammography image. Because of this, the position of the coronal image closest to the thoracic cavity can be regarded as the position of the chest wall. As illustrated in FIG. 12, for example, the second detection unit 248d detects the position of the coronal image closest to the body surface (the lower side in FIG. 12) among a plurality of coronal images that can be generated from the second volume data as a position $Y_{mw}$ of the chest wall.

The second detection unit 248d conducts a search in the brightness values of the voxels contained in the second volume data, starting with the side opposite the thoracic cavity and detects a position whose brightness value has first exceeded a certain threshold as the position of the nipple. For example, the second detection unit 248d conducts a search in the brightness values of the voxels contained in the second volume data, starting with the side opposite the thoracic cavity (the upper side in FIG. 12) in the $X_m$ axial direction and the $Z_m$ axial direction, and performs this searching in the $X_m$ axial direction and the $Z_m$ axial direction successively in the $Y_m$ axial direction. The second detection unit 248d detects a position whose brightness value has first exceeded zero as a position $Y_{mn}$ of the nipple in the second volume data.

Figure 13:
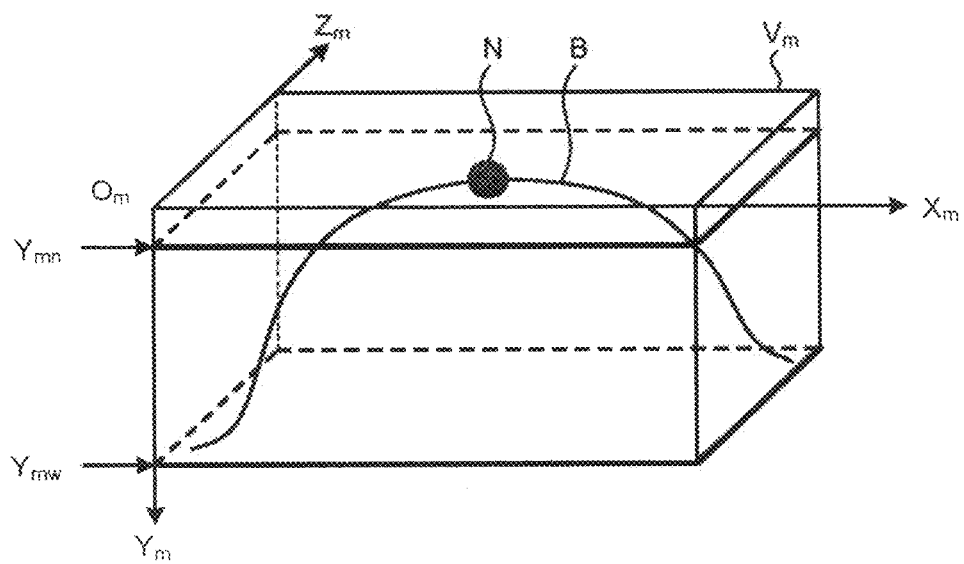
FIG. 13 is a diagram illustrating an example of a chest wall and a nipple detected by the second detection unit according to the first embodiment.

FIG. 13 is a diagram illustrating an example of the chest wall and the nipple detected by the second detection unit 248*d* according to the first embodiment. As illustrated in FIG. 13, the second detection unit 248*d* detects the position $Y_{mw}$ of the chest wall and the position $Y_{mn}$ of the nipple in the depth direction (the $Y_m$ axial direction) based on the second volume data $V_m$ illustrated in FIG. 11.

Although described is an example of a case in which the second detection unit 248*d* automatically detects the positions of the chest wall and the nipple, that is not limiting; for example, the second detection unit 248*d* may accept operation designating the positions of the chest wall and the nipple from the operator via the input device 22, thereby detecting the positions of the chest wall and the nipple in the second volume data.

In this case, for example, the second detection unit 248*d* generates a plurality of coronal images based on the second volume data and causes the display 23 to display the generated coronal images in order in accordance with operation by the operator. The second detection unit 248*d* accepts operation to select a coronal image to be the section of the chest wall from the displayed coronal images from the operator and detects the position of the section selected by the operation as the position $Y_{mw}$ of the chest wall. Similarly, the second detection unit 248*d* accepts operation to select a coronal image to be the section of the nipple from the operator and detects the position of the section selected by the operation as the position $Y_{mn}$ of the nipple.

Returning back to FIG. 5, the second generating unit 248*e* generates the second sectional image based on the second volume data. Specifically, the second generating unit 248*e* reads the second volume data on the subject to be diagnosed from the second data storage 246*a* and generates the second sectional image based on the second volume data. For example, the second generating unit 248*e* generates the second sectional image by performing the MPR reconstruction using the second volume data.

Figure 14:
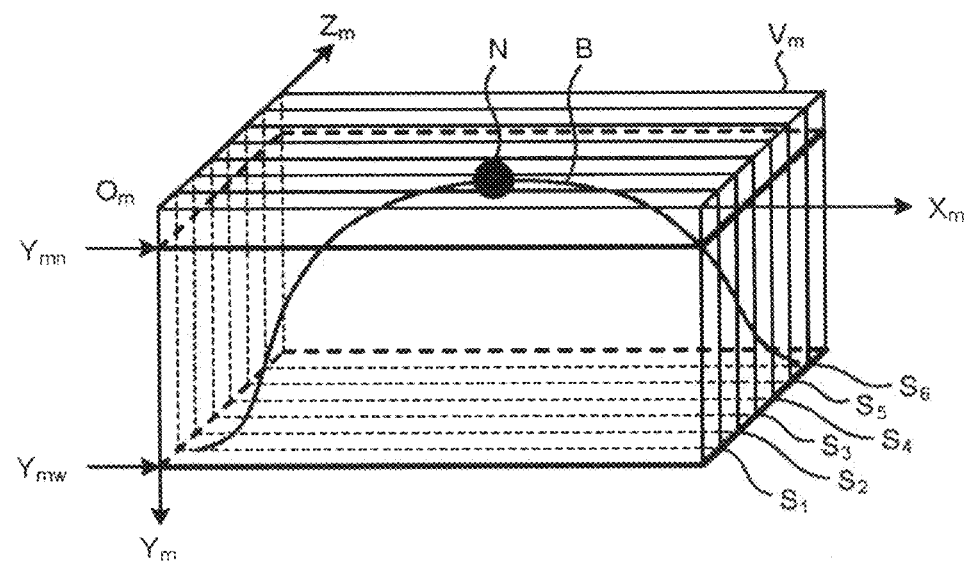
FIG. 14 is a diagram illustrating an example of the generation of a second sectional image by a second generating unit according to the first embodiment.

FIG. 14 is a diagram illustrating an example of the generation of the second sectional image by the second generating unit 248*e* according to the first embodiment. As illustrated in FIG. 14, for example, the second generating unit 248*e* generates as the second sectional image a plurality of axial images $S_1$ to $S_6$. In this situation, for example, the second generating unit 248*e* generates the axial images at certain intervals in the $Z_m$ axial direction. The second generating unit 248*e* may generate as the second sectional image sagittal images or may generate other sectional images orthogonal to the coronal images.

Figure 15:
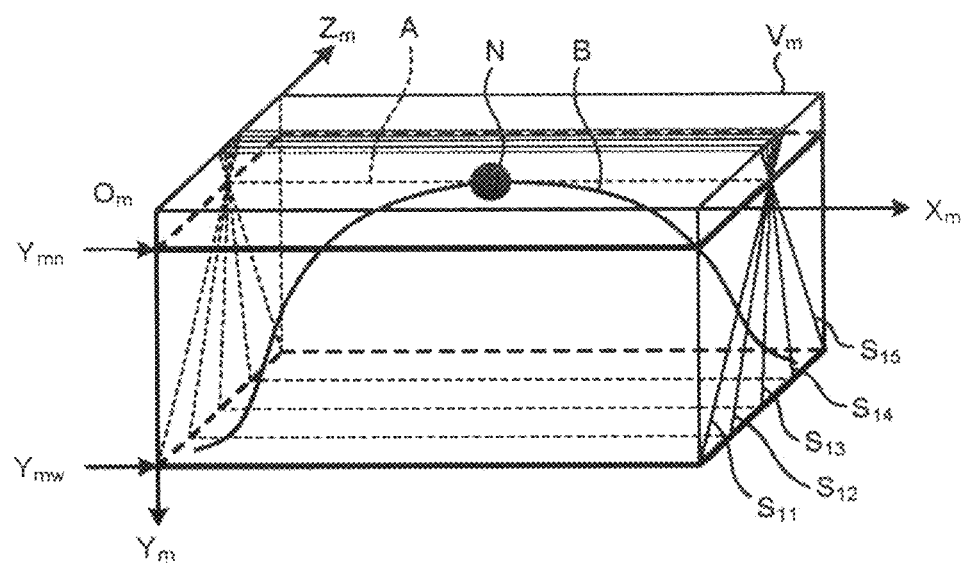
FIG. 15 is a diagram illustrating another example of the generation of a second sectional image by the second generating unit according to the first embodiment.

FIG. 15 is a diagram illustrating another example of the generation of the second sectional image by the second generating unit 248*e* according to the first embodiment. For example, the second generating unit 248*e* may generate as the second sectional image a plurality of sectional images passing through the nipple N. In this situation, as illustrated in FIG. 15, for example, the second generating unit 248*e* generates a plurality of sectional images $S_{11}$ to $S_{15}$ containing a line A passing through the nipple N parallel to the $X_m$ axis. In this situation, for example, the second generating unit 248*e* generates the sectional images so that they are staggered in gradient by a certain angle with the line A as the central axis.

Returning back to FIG. 5, the display control unit 248*f* causes the display 23 to display the first sectional image generated based on the first volume data as the three-dimensional ultrasonic image data obtained by imaging the breast B and the second sectional image generated based on the second volume data as the three-dimensional mammography image data obtained by imaging the breast B. Specifically, the display control unit 248*f* causes the display 23 to display the first sectional image generated by the first generating unit 248*c* and the second sectional image generated by the second generating unit 248*e*.

The display control unit 248*f* causes the display 23 to further display information indicating the positional relation of the breast B drawn in the respective first and second sectional images based on the positions of the chest wall and the nipple in the respective first and second volume data. Specifically, the display control unit 248*f* causes the display 23 to display information indicating the positional relation of the breast B drawn in the respective first and second sectional images based on the positions of the chest wall and the nipple detected by the first detection unit 248*b* and the positions of the chest wall and the nipple detected by the second detection unit 248*d*.

For example, the display control unit 248*f* displays a mark as the information indicating the positional relation. Examples of the mark described in this example include graphics of various shapes such as lines and annotations including text information.

Figure 16:
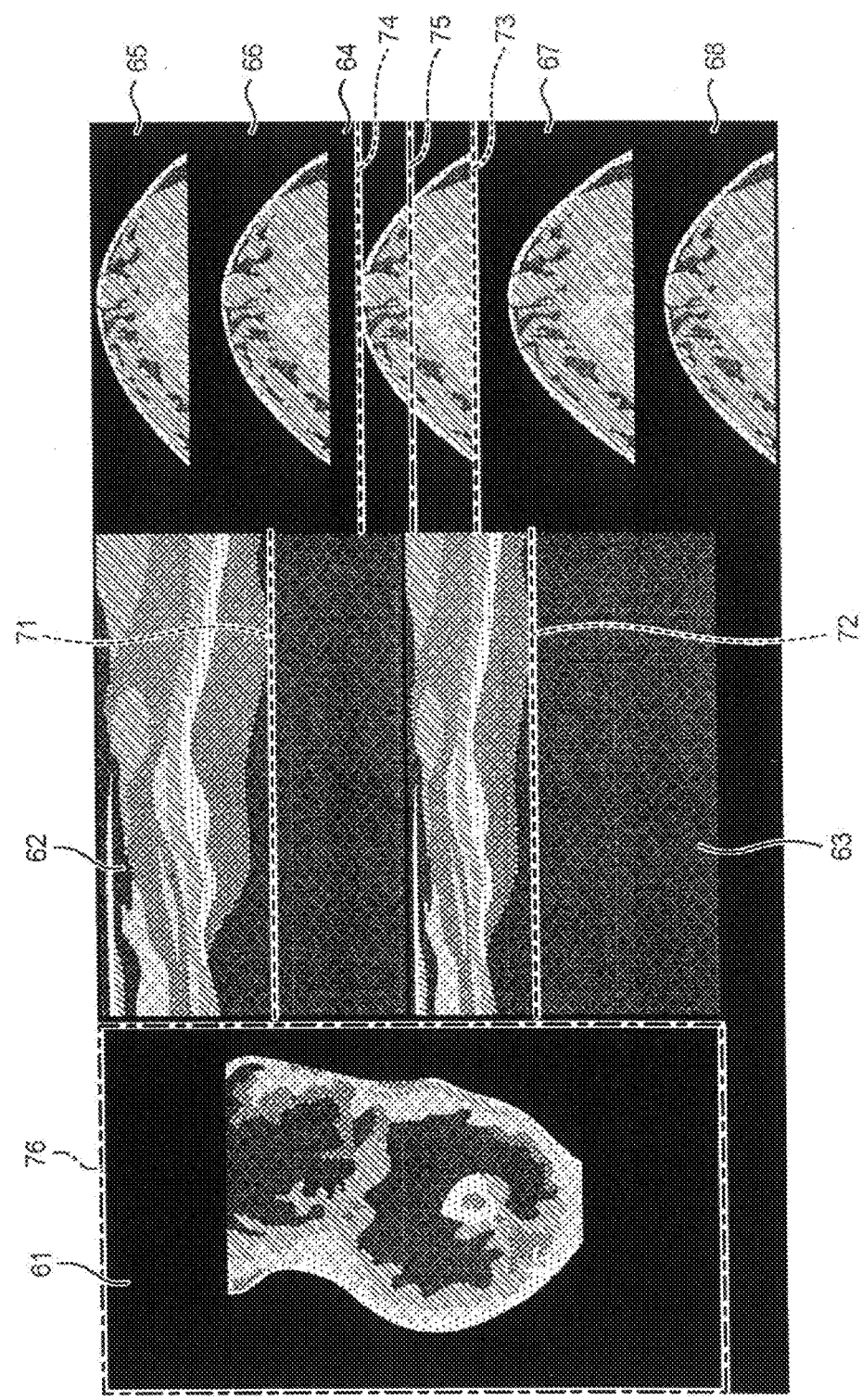
FIG. 16 is a diagram illustrating an example of the display of sectional images by a display control unit according to the first embodiment.

FIG. 16 is a diagram illustrating an example of the display of sectional images by the display control unit 248*f* according to the first embodiment. As illustrated in FIG. 16, for example, the display control unit 248*f* causes the display 23 to display a coronal image 61 generated by the first generating unit 248*c* and an axial image 62 and a sagittal image 63 generated by the image processor 244 from the first volume data.

Furthermore, for example, the display control unit 248*f* causes the display 23 to display an axial image 64 generated by the second generating unit 248*e* from the second volume data. The display control unit 248*f* causes a plurality of axial images 65 to 68 to be displayed beside the axial image 64. The display control unit 248*f* may display the sectional images passing through the nipple N illustrated in FIG. 15 in place of the axial images 64 to 68.

For example, the display control unit 248*f* displays a line 71 indicating the position of the chest wall detected by the first detection unit 248*b* on the axial image 62 generated from the first volume data. The display control unit 248*f* displays a line 72 indicating the position of the chest wall detected by the first detection unit 248*b* on the sagittal image 63 generated from the first volume data.

For example, the display control unit 248*f* displays a line 73 indicating the position of the chest wall detected by the second detection unit 248*d* and a line 74 indicating position of the nipple detected by the second detection unit 248*d* on the axial image 64 generated from the second volume data. The display control unit 248*f* may display the line 73 indicating the position of the chest wall and the line 74 indicating the position of the nipple also on the other axial images 65 to 68 similarly.

For example, the display control unit 248*f* displays a line 75 indicating the position of the coronal image 61 generated from the first volume data on the axial image 64 generated from the second volume data. For example, the display control unit 248*f* displays a line 76 in the same display manner as the line 75 around the coronal image 61. This display enables the operator to intuitively grasp the positional relation between the coronal image imaged by the ultrasonic diagnostic apparatus 20 and the axial image imaged by the mammography apparatus 10.

Figure 17:
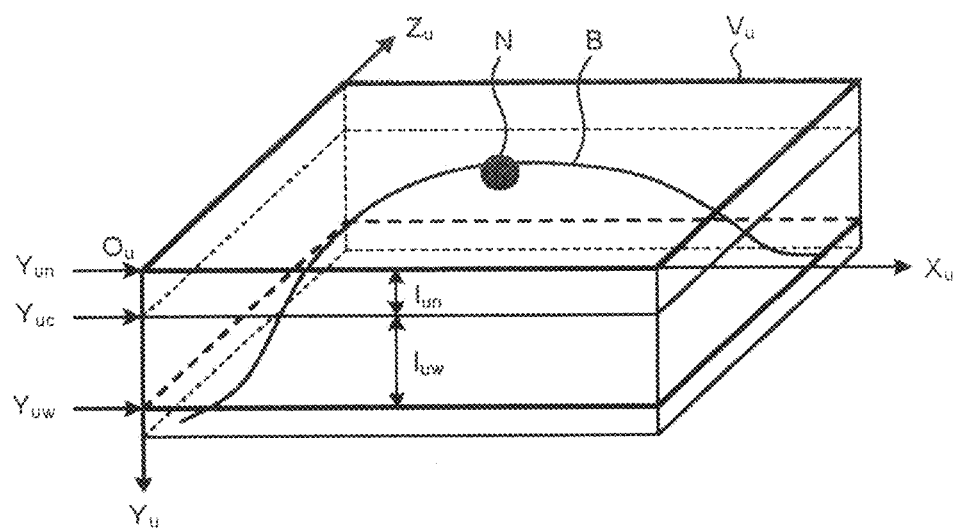
FIGS. 17 and 18 are diagrams illustrating an example of the display of the positional relation of sectional images by the display control unit according to the first embodiment.
Figure 18:
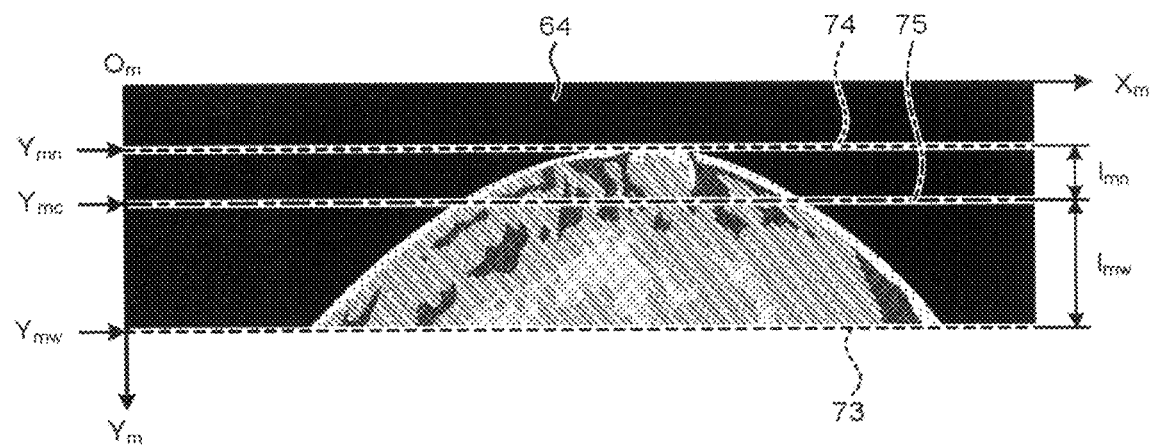

FIGS. 17 and 18 are diagrams illustrating an example of the display of the positional relation of sectional images by the display control unit 248*f* according to the first embodiment. As illustrated in FIG. 17, for example, it is assumed that in the first volume data $V_u$ the position of the coronal image 61 illustrated in FIG. 16 is $Y_{uc}$. In this case, as illustrated in FIG. 18, for example, the display control unit 248f displays the line 75 indicating the position of the coronal image 61 at a position $Y_{mc}$ that causes the length $l_{mw}$ of $Y_{mw}$ to $Y_{mc}$: the length $l_{mn}$ of $Y_{mn}$ to $Y_{mc}$=the length $l_{uw}$ of $Y_{uw}$ to $Y_{uc}$: the length $l_{un}$ of $Y_{un}$ to $Y_{uc}$ when the position of the chest wall is $Y_{mw}$, and the position of the nipple N is $Y_{mn}$ on the axial image 64.

Although FIG. 16 illustrates an example of a case in which the display control unit 248f displays one coronal image 61 generated by the first generating unit 248c, that is not limiting; for example, the display control unit 248f may display a plurality of coronal images 61.

Figure 19:
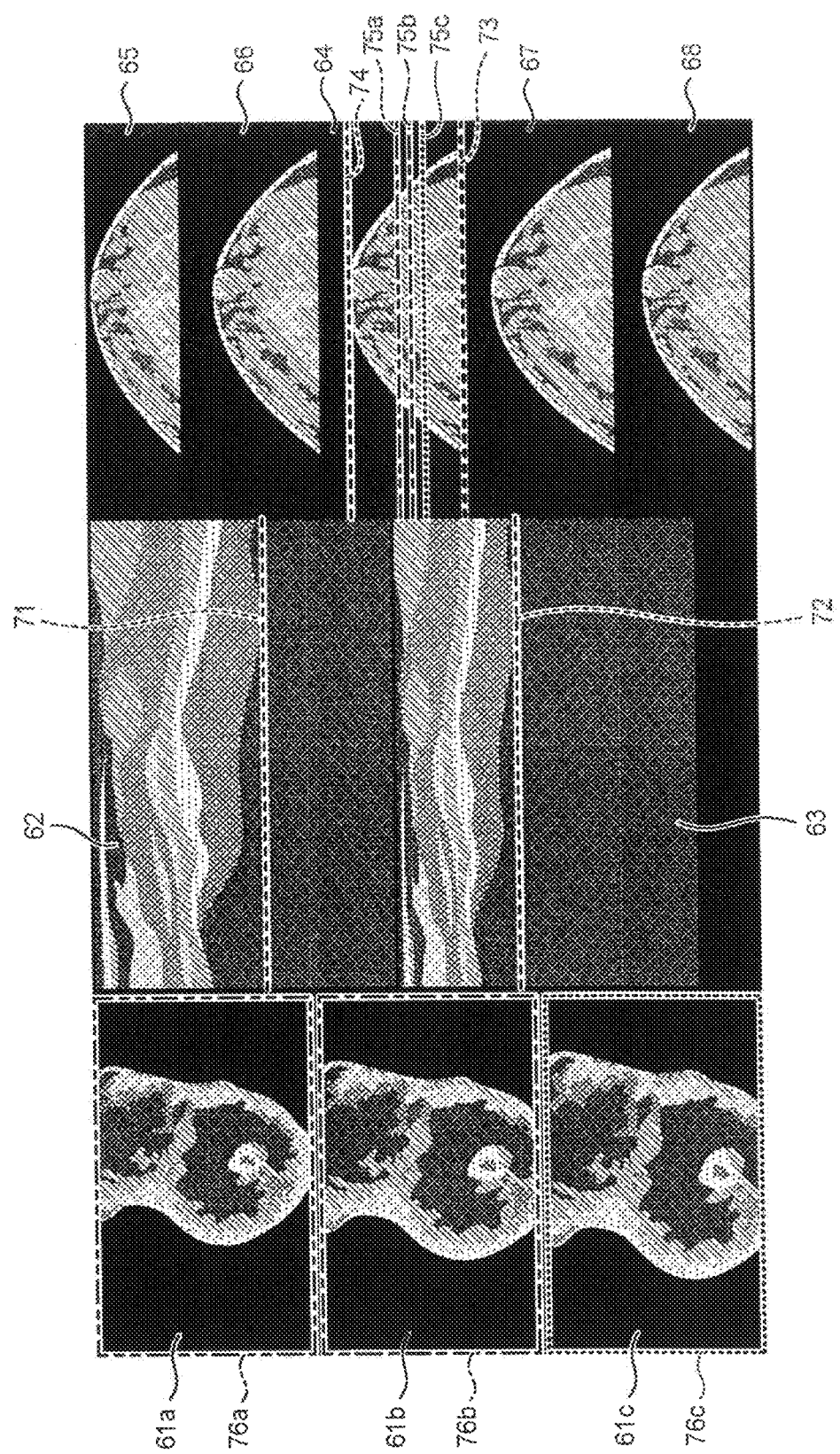
FIG. 19 is a diagram illustrating another example of the display of sectional images by the display control unit according to the first embodiment.

FIG. 19 is a diagram illustrating another example of the display of sectional images by the display control unit 248f according to the first embodiment. As illustrated in FIG. 19, for example, the display control unit 248f causes the display 23 to display three coronal images 61a to 61c generated by the first generating unit 248c. In this case, for example, the display control unit 248f displays a line 75a indicating the position of the coronal image 61a, a line 75b indicating the position of the coronal image 61b, and a line 75c indicating the position of the coronal image 61c on the axial image 64.

For example, the display control unit 248f displays a line 76a in the same display manner as the line 75a around the coronal image 61a, a line 76b in the same display manner as the line 75b around the coronal image 61b, and a line 76c in the same display manner as the line 75c around the coronal image 61c. This display enables the operator to intuitively grasp the positional relation between the respective coronal images and the axial image imaged by the mammography apparatus 10 even when a plurality of coronal images imaged by the ultrasonic diagnostic apparatus 20 are displayed.

Figure 20:
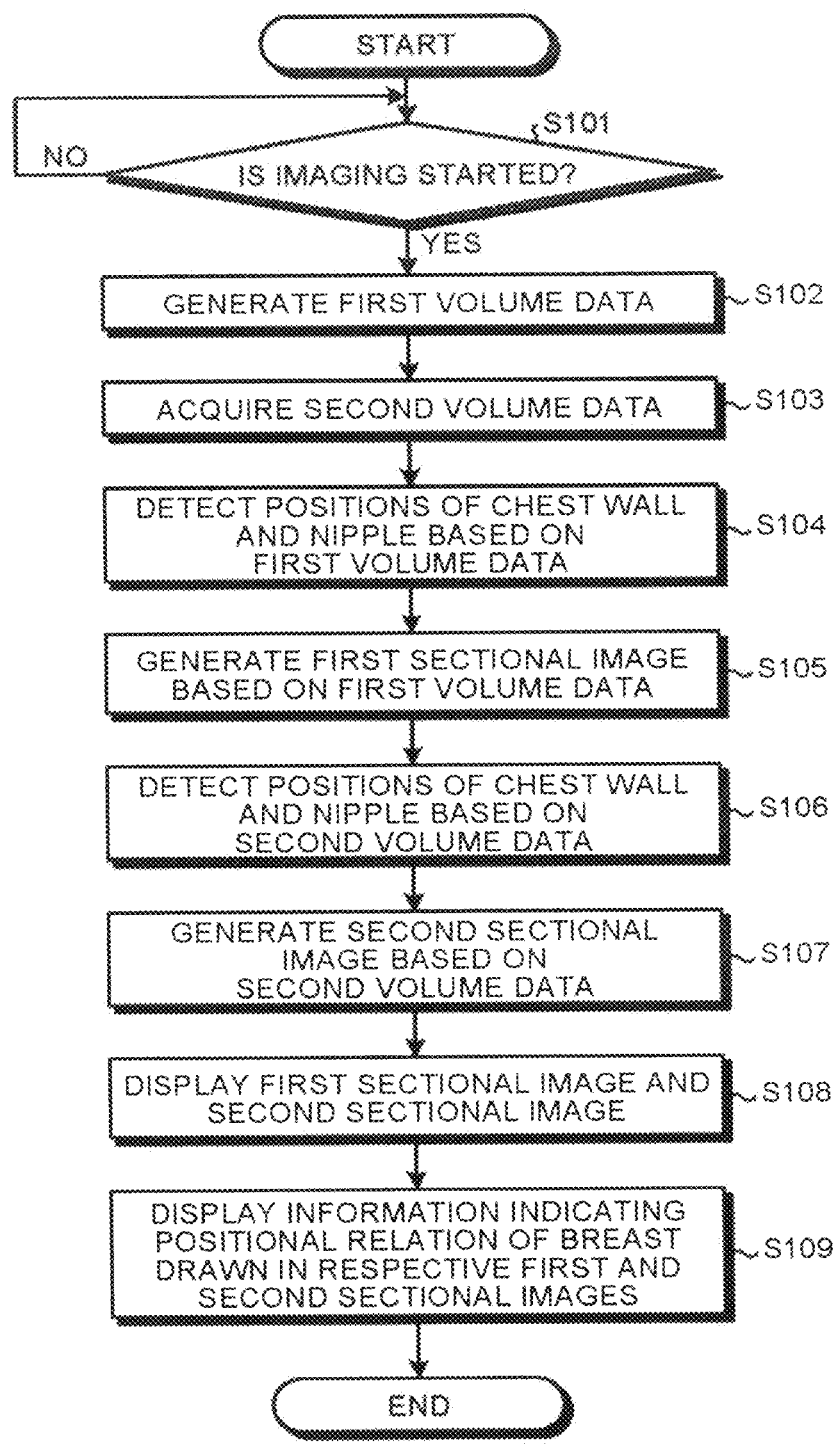
FIG. 20 is a flowchart illustrating the processing procedures of processing by the ultrasonic diagnostic apparatus according to the first embodiment.

FIG. 20 is a flowchart illustrating the processing procedures of processing by the ultrasonic diagnostic apparatus 20 according to the first embodiment. As illustrated in FIG. 20, for example, in the ultrasonic diagnostic apparatus 20 according to the present embodiment, when the controller 248 accepts an instruction to start imaging from the operator via the input device 22 (Yes at Step S101), the following processing is started.

First, the image processor 244 generates the first volume data as the three-dimensional ultrasonic image data obtained by imaging the breast of the subject based on the data collected by scanning the breast of the subject by the ultrasonic probe 21 (Step S102). The data acquisition unit 248a acquires the second volume data as the three-dimensional mammography image data obtained by imaging the breast of the same subject (Step S103).

Based on the first volume data, the first detection unit 248b detects the positions of the chest wall and the nipple in the first volume data (Step S104). The first generating unit 248c generates the first sectional image based on the first volume data (Step S105).

Based on the second volume data, the second detection unit 248d detects the positions of the chest wall and the nipple in the second volume data (Step S106). The second generating unit 248e generates the second sectional image based on the second volume data (Step S107).

After that, the display control unit 248f causes the display 23 to display the first sectional image and the second sectional image (Step S108). Furthermore, the display control unit 248f causes the display 23 to display information indicating the positional relation of the breast drawn in the respective first and second sectional images based on the positions of the chest wall and the nipple in the respective first and second volume data (Step S109).

The processing procedures of the processing by the ultrasonic diagnostic apparatus 20 is not limited to the one illustrated in FIG. 20; for example, the data acquisition unit 248a may acquire the second volume data before the controller 248 accepts the instruction to start imaging from the operator. For example, when the second volume data is imaged by the mammography apparatus 10, the data acquisition unit 248a may acquire the second volume data from the mammography apparatus 10 or the medical image processing apparatus 30.

For example, the position detection of the chest wall and the nipple by the first detection unit 248b and the position detection of the chest wall and the nipple by the second detection unit 248d may be processed in the reverse order or may be processed in parallel. The generation of the first sectional image by the first generating unit 248c and the generation of the second sectional image by the second generating unit 248e may also be processed in the reverse order or may be processed in parallel.

As described above, in the first embodiment, the ultrasonic diagnostic apparatus 20 displays the first sectional image generated based on the three-dimensional ultrasonic image data and the second sectional image generated based on the three-dimensional mammography image data together with the information indicating the positional relation of the breast drawn in the respective sectional images. The present embodiment can therefore, when mammary gland image diagnosis is performed by the ultrasonic diagnostic apparatus 20, for example, easily compare the ultrasonic image and the mammography image. This comparison enables a load related to interpretation in the mammary gland image diagnosis that uses both the three-dimensional ultrasonic image data and the three-dimensional mammography image data in combination.

Second Embodiment

A medical image processing apparatus according to the second embodiment includes a detection unit, a generating unit, an associating unit, and a display. The detection unit analyzes a first piece of image data obtained by imaging a breast of a subject and a second piece of image data obtained by imaging the breast and detects the positions of a chest wall and a nipple in each of the pieces of image data, wherein the first piece of image data is three-dimensional medical image data and the second piece of image data is medical image data of a different type from the first piece of image data. The generating unit generates a first sectional image based on the first piece of image data and generates a second sectional image based on the second piece of image data. The associating unit associates the positional relation of the breast in the first piece of image data and the second piece of image data so that the positions of the chest wall and the nipple match between the first and the second pieces of image data. The display displays the first sectional image, the second sectional image, and a mark indicating the positional relation of the breast.

The second embodiment describes an example of a case in which the first piece of image data is three-dimensional ultrasonic images, whereas the second piece of image data is three-dimensional mammography image data. The medical image processing apparatus 30 according to the second embodiment includes a first detection unit and a second detection unit as the above detection unit, includes a first generating unit and a second generating unit as the above generating unit, and includes a display control unit as the above associating unit.

The first embodiment describes an example of a case in which the ultrasonic diagnostic apparatus 20 displays the first sectional image generated based on the three-dimensional ultrasonic image data and the second sectional image generated based on the three-dimensional mammography image data. Meanwhile, the second embodiment describes an example of a case in which the medical image processing apparatus 30 displays the first sectional image and the second sectional image. The configuration of the apparatuses of the medical image processing system according to the second embodiment is the same as the one illustrated in FIG. 1.

Figure 21:
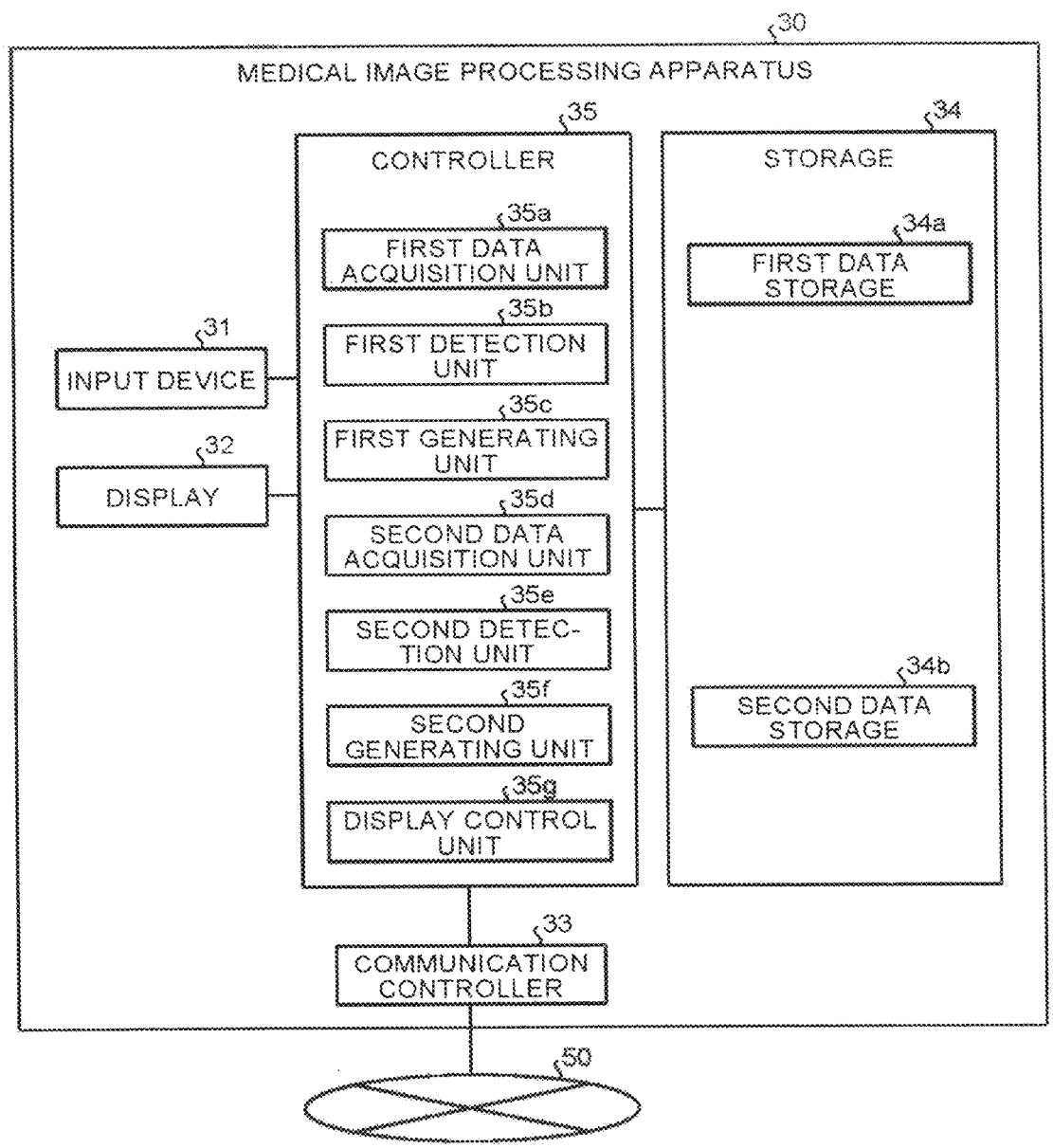
FIG. 21 is a diagram illustrating a configuration example of a medical image processing apparatus according to a second embodiment.

FIG. 21 is a diagram illustrating a configuration example of the medical image processing apparatus 30 according to a second embodiment. As illustrated in FIG. 21, the medical image processing apparatus 30 includes an input device 31, a display 32, a communication controller 33, a storage 34, and a controller 35.

The input device 31 accepts various kinds of operations and various kinds of information from an operator. The input device is, for example, a keyboard, a mouse, a button, a trackball, or a touch panel.

The display 32 displays a GUI and various kinds of screens for accepting the various kinds of operations from the operator. The display 32 is, for example, a liquid crystal display, a cathode ray tube (CRT) display, or a touch panel.

The communication controller 33 controls communication performed with the other apparatuses via the network 50. The communication controller 33 is, for example, a network card or a network adapter and connects to the network 50 via a LAN such as Ethernet (registered trademark) to perform communication with the other apparatuses. For example, the communication controller 33 connects to the network 50 via a wireless LAN to perform wireless communication with the other apparatuses.

The storage 34 is a storage device such as a hard disk and a semiconductor memory to store therein various kinds of information. Specifically, the storage 34 includes a first data storage 34a and a second data storage 34b.

The first data storage 34a stores therein first volume data as three-dimensional ultrasonic image data obtained by imaging a breast of a subject. The first volume data is acquired by a first data acquisition unit 35a described below and is stored in the first data storage 34a.

The second data storage 34b stores therein second volume data as three-dimensional mammography image data obtained by imaging the breast of the subject. The second volume data is acquired by a second data acquisition unit 35d described below and is stored in the second data storage 34b.

The controller 35 includes a CPU and a memory and executes various kinds of programs using them to control the operation of the medical image processing apparatus 30. Specifically, the controller 35 includes the first data acquisition unit 35a, a first detection unit 35b, a first generating unit 35c, the second data acquisition unit 35d, a second detection unit 35e, a second generating unit 35f, and a display control unit 35g.

The first data acquisition unit 35a acquires the first volume data as the three-dimensional ultrasonic image data obtained by imaging the breast of the subject. Specifically, the first data acquisition unit 35a acquires the first volume data from the ultrasonic diagnostic apparatus 20 via the communication controller 33 and stores it in the first data storage 34a.

Based on the first volume data as the three-dimensional ultrasonic image data obtained by imaging the breast of the subject, the first detection unit 35b detects the positions of a chest wall and a nipple in the first volume data. For example, the first detection unit 35b detects the positions of the chest wall and the nipple in the first volume data based on the first volume data stored in the first data storage 34a in a similar manner to the first detection unit 248b described in the first embodiment.

The first generating unit 35c generates the first sectional image based on the first volume data. For example, the first generating unit 35c generates the first sectional image based on the first volume data stored in the first data storage 34a in a similar manner to the first generating unit 248c described in the first embodiment.

The second data acquisition unit 35d acquires the second volume data as the three-dimensional mammography image data obtained by imaging the breast of the subject. Specifically, the second data acquisition unit 35d acquires the second volume data from the mammography apparatus 10 via the communication controller 33 and stores it in the second data storage 34b.

Based on the second volume data as the three-dimensional mammography image data obtained by imaging the breast of the subject, the second detection unit 35e detects the positions of the chest wall and the nipple in the second volume data. For example, the second detection unit 35e detects the positions of the chest wall and the nipple in the second volume data based on the second volume data stored in the second data storage 34b in a similar manner to the second detection unit 248d described in the first embodiment.

The second generating unit 35f generates the second sectional image based on the second volume data as the three-dimensional mammography image data obtained by imaging the breast of the subject. For example, the second generating unit 35f generates the second sectional image based on the second volume data stored in the second data storage 34b in a similar manner to the second generating unit 248e described in the first embodiment.

The display control unit 35g causes the display 32 to display the first sectional image generated based on the first volume data as the three-dimensional ultrasonic image data obtained by imaging the breast and the second sectional image generated based on the second volume data as the three-dimensional mammography image data obtained by imaging the breast. For example, the display control unit 35g causes the display 32 to display the first sectional image generated by the first generating unit 35c and the second sectional image generated by the second generating unit 35f in a similar manner to the display control unit 248f described in the first embodiment.

The display control unit 35g causes the display 32 to further display information indicating the positional relation of the breast drawn in the respective first and second sectional images based on the positions of the chest wall and the nipple in the respective first and second volume data. For example, the display control unit 35g causes the display 32 to display information indicating the positional relation of the breast drawn in the respective first and second sectional images based on the positions of the chest wall and the nipple detected by the first detection unit 35b and the positions of the chest wall and the nipple detected by the second detection unit 35e in a similar manner to the display control unit 248f described in the first embodiment.

As described above, in the second embodiment, the medical image processing apparatus 30 displays the first sectional image generated based on the three-dimensional ultrasonic image data and the second sectional image generated based on the three-dimensional mammography image data together with the information indicating the positional relation of the breast drawn in the respective sectional images. The present embodiment can therefore, when mammary gland image diagnosis is performed by the medical image processing apparatus 30, easily compare the ultrasonic image and the mammography image. This comparison can reduce a load related to interpretation in the mammary gland image diagnosis that uses both the three-dimensional ultrasonic image data and the three-dimensional mammography image data in combination.

Other Embodiments

The respective components of the respective apparatuses described in the above embodiments are functionally conceptual, and it is not necessarily required that they be physically configured as illustrated. In other words, the specific forms of the respective apparatuses are not limited to the illustrated ones, and the whole or part thereof may be configured through functional or physical distribution or integration on an arbitrary unit in accordance with various kinds of loads and use conditions.

For example, among the respective units described as included in the ultrasonic diagnostic apparatus 20 in the first embodiment, the second detection unit and the second generating unit that process the second volume data may be installed in the mammography apparatus 10. In this case, for example, the data acquisition unit of the ultrasonic diagnostic apparatus 20 acquires the second sectional image generated based on the second volume data and the information indicating the positions of the chest wall and the nipple in the second volume data from the mammography apparatus 10. In this case, for example, the mammography apparatus 10 may transmit only a sectional image selected by the operator among a plurality of second sectional images generated by the second generating unit to the ultrasonic diagnostic apparatus 20. This processing, for example, enables only a sectional image determined to be characteristic by the operator to be transmitted to the ultrasonic diagnostic apparatus 20 and can perform image diagnosis using the ultrasonic diagnostic apparatus 20 more efficiently.

The display control unit described in the first and second embodiments may be installed in the image display apparatus 40. In this case, for example, the image display apparatus 40 acquires the first sectional image from the first generating unit installed in the ultrasonic diagnostic apparatus 20 or the medical image processing apparatus 30 and acquires the information indicating the positions of the chest wall and the nipple in the first volume data from the first detection unit installed in the ultrasonic diagnostic apparatus 20 or the medical image processing apparatus 30. The image display apparatus 40 acquires the second sectional image from the second generating unit installed in the mammography apparatus 10 or the medical image processing apparatus 30 and acquires the information indicating the positions of the chest wall and the nipple in the first volume data from the second detection unit installed in the mammography apparatus 10 or the medical image processing apparatus 30.

Although the above embodiment describes an example of a case in which the generating unit (the second generating unit) generates a plurality of sectional images (axial images, for example) at regular intervals, that is not limiting; for example, the generating unit may generate the first sectional image and the second sectional image corresponding to mutually the same position based on the positional relation of the breast associated between the first piece of image data and the second piece of image data.

For example, the display control unit accepts the designation of a position for the second sectional image displayed on the display, from the operator via the input device. The generating unit then identifies a position corresponding to the position designated by the operator in the three-dimensional ultrasonic image data based on the above positional relation of the breast and generates a sectional image corresponding to the identified position as the first sectional image. On the contrary, the generating unit may accept the designation of a position for the first sectional image from the operator and generate the second sectional image corresponding to the accepted position based on the second piece of image data.

Figure 22:
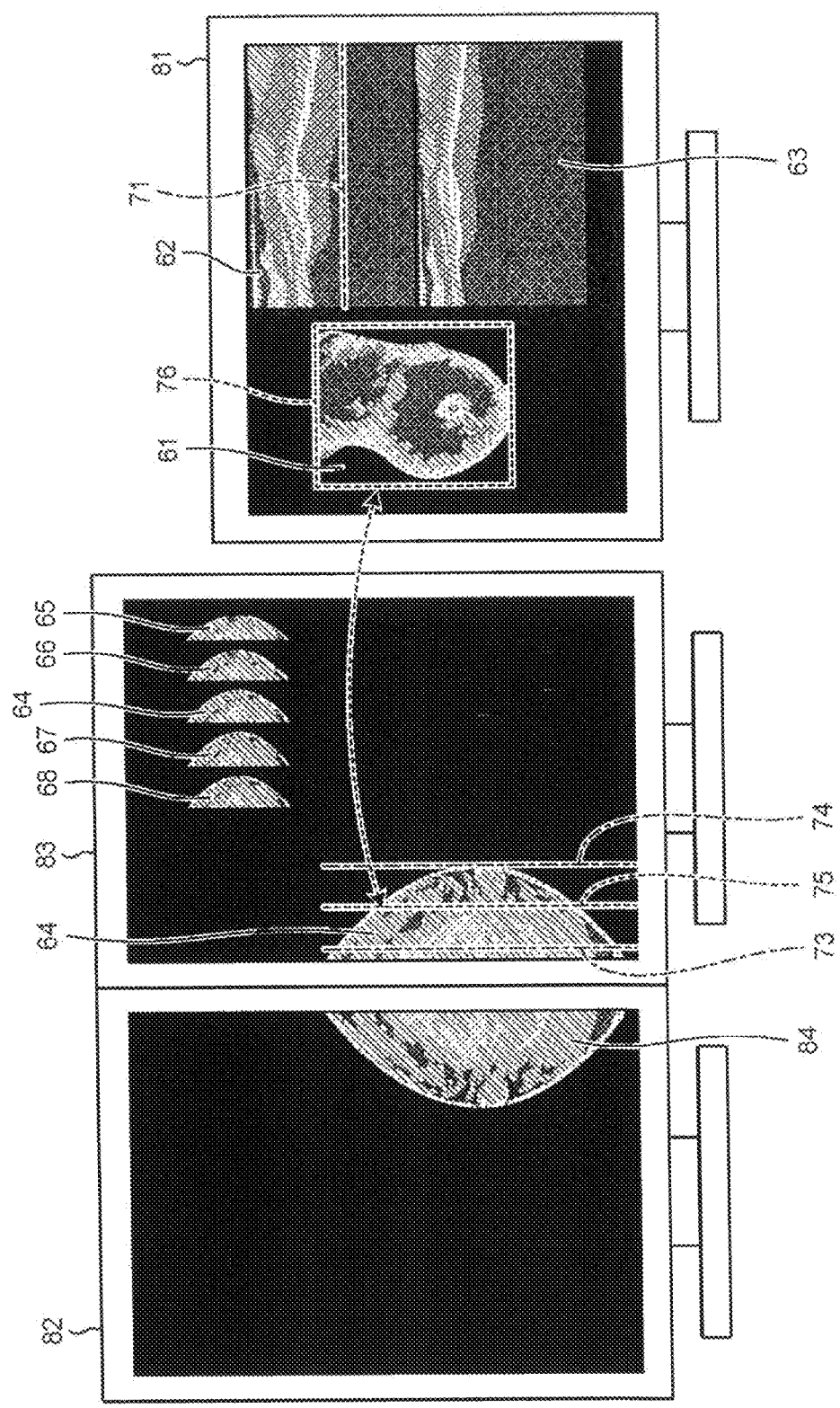
FIG. 22 is a diagram illustrating an example of displays of sectional images realized by a display control unit according to another embodiment.

FIG. 22 is a diagram illustrating an example of displays of sectional images realized by a display control unit according to another embodiment. The present embodiment will be explained by using a medical image processing apparatus as an example, similarly to the second embodiment. Also, the present embodiment describes the example in which, similarly to the second embodiment, the first piece of image data (the first volume data) is three-dimensional ultrasonic image data, whereas the second piece of image data (the second volume data) is three-dimensional mammography image data.

Similarly to the second embodiment, the medical image processing apparatus according to the present embodiment includes a first detection unit and a second detection unit (the detection unit), a first generating unit and a second generating unit (the generating unit), a display control unit (the associating unit), and a display.

Further, in the present embodiment, the medical image processing apparatus includes a first monitor, a second monitor, and a third monitor, as the display. In this situation, the first monitor is a monitor used for displaying an ultrasonic image, whereas the second and the third monitors are monitors used for displaying mammography images. For example, the first monitor may be configured with a monitor having a common resolution level that is installed with a personal computer or the like. Further, for example, the second and the third monitors may each be configured with a monitor having a high resolution level (e.g., approximately 5 megapixels) approved for medical use.

Further, for example, as illustrated in FIG. 22, the display control unit causes a first monitor 81 to display a coronal image 61 of a breast generated from the first volume data represented by three-dimensional ultrasonic image data and an axial image 62 and a sagittal image 63 of the breast that are also generated from the first volume data.

Further, the display control unit causes a second monitor 82 and a third monitor 83 to each display a Craniocaudal (CC) image of the breast generated from the second volume data represented by three-dimensional mammography image data. For example, as illustrated in FIG. 22, when the second monitor 82 and the third monitor 83 are arranged next to each other in the left-and-right direction as viewed by the operator, the display control unit displays the CC image of the right breast on the second monitor 82 positioned on the left and displays the CC image of the left breast on the third monitor 83 positioned on the right.

For example, in response to an instruction from the operator, the display control unit displays a plurality of axial images 64 to 68 of the left breast that are reduced in size and arranged next to each other in an upper section of the third monitor 83. Further, when the operator has selected one of the displayed reduced CC images 64 to 68, the display control unit displays the selected axial image in a lower section of the third monitor 83. For example, as illustrated in FIG. 22, the display control unit displays the CC image 64 in the lower section of the third monitor 83. Similarly, the display control unit displays a CC image 84 of the right breast in a lower section of the second monitor 82. As a result, the mammography images of the left breast and the right breast are displayed while being arranged next to each other.

Further, for example, as illustrated in FIG. 22, the display control unit displays a line 71 indicating the position of the chest wall detected by the first detection unit, in the axial image 62 of the ultrasonic image displayed on the first monitor 81. In the sagittal image 63, the display control unit may or may not display a line indicating the position of the chest wall.

Further, in the CC image 64 of the mammography image displayed on the third monitor 83, the display control unit displays a line 73 indicating the position of the chest wall detected by the second detection unit and a line 74 indicating the position of the nipple detected by the second detection unit.

Further, in the CC image 64, the display control unit displays a line 75 indicating the position of the coronal image 61 of the ultrasonic image displayed on the first monitor 81. In this situation, for example, the display control unit also displays another line 76 around the coronal image 61, in the same display manner as the line 75. This display enables the operator to intuitively grasp the positional relation between the coronal image imaged by the ultrasonic diagnostic apparatus and the CC image imaged by the mammography apparatus (see the two-way broken-line arrow in FIG. 22).

After that, the display control unit accepts a designation of a position for the CC image 64 of the mammography image displayed on the third monitor 83, from the operator via the input device. For example, as the operation to designate the position, the display control unit accepts an operation to move the line 75 displayed in the axial image 64 in a direction toward the chest wall or in a direction toward the nipple.

When the operation is accepted, the display control unit moves the line 75 to the position designated by the operator, within the CC image 64 displayed on the third monitor 83.

Further, when the operation is accepted, the first generating unit identifies a position corresponding to the position designated by the operator, in the first volume data represented by the three-dimensional ultrasonic image data. At that time, the first generating unit identifies the position corresponding to the designated position, based on the positions of the chest wall and the nipple detected by the first detection unit. Further, the first generating unit generates a coronal image of the identified position. In that situation, if a plurality of coronal images have already been generated and stored in a storage, the first generating unit reads one of the coronal images corresponding to the designated position from the storage. After that, the display control unit causes the first monitor to display the coronal image either generated or read by the first generating unit, so as to replace the coronal image 61 that was displayed previously. As a result, the ultrasonic image corresponding to the designated position is displayed on the first monitor 81 in conjunction with the designation of the position made in the mammography image displayed on the third monitor 83.

In addition, the display control unit accepts, via the input device, an operation to replace the coronal image 61 of the ultrasonic image displayed on the first monitor 81 with a coronal image corresponding to another position generated from the same volume data.

When the operation is accepted, the first generating unit either generates from the first volume data or reads from the storage, the coronal image corresponding to the position designated by the operator. After that, the display control unit causes the first monitor 81 to display the coronal image either generated or read by the first generating unit, so as to replace the coronal image 61 that was displayed previously.

Further, when the operation is accepted, the display control unit identifies the position corresponding to the coronal image newly displayed on the first monitor 81, in the CC image 64 of the mammography image displayed on the third monitor 83. At that time, in the CC image 64, the display control unit identifies the position corresponding to the coronal image of the newly-displayed ultrasonic image, based on the positions of the chest wall and the nipple detected by the second detection unit. Further, the display control unit moves the line 75 indicating the position of the coronal image 61 of the ultrasonic image displayed on the first monitor 81, to the position identified in the CC image 64. As a result, the position of the newly-displayed coronal image is indicated in the mammography image displayed on the third monitor 83, in conjunction with the replacing operation performed on the coronal image of the ultrasonic image displayed on the first monitor 81.

The description above explains the example with the conjunctive display between the ultrasonic image displayed on the first monitor 81 and the mammography image of the left breast displayed on the third monitor 83; however, possible embodiments are not limited to this example. For instance, the ultrasonic image displayed on the second monitor 82 may be displayed in conjunction with the mammography image of the right breast displayed on the third monitor 83.

Further, although the above description explains the example in which the plurality of monitors are used, possible embodiments are not limited to this example. For instance, there may be situations of conferences to discuss medical examination plans and treatment plans or training sessions where a plurality of medical doctors have a discussion while a plurality of medical images of a subject imaged by a plurality of mutually-different medical image diagnostic apparatuses are displayed on a single monitor and while the medical doctors refer to the plurality of displayed medical images, image interpretation reports, and the like. In those situations, a large-sized general-purpose monitor is used so that the plurality of doctors are able to refer to the plurality of medical images at the same time.

Figure 23:
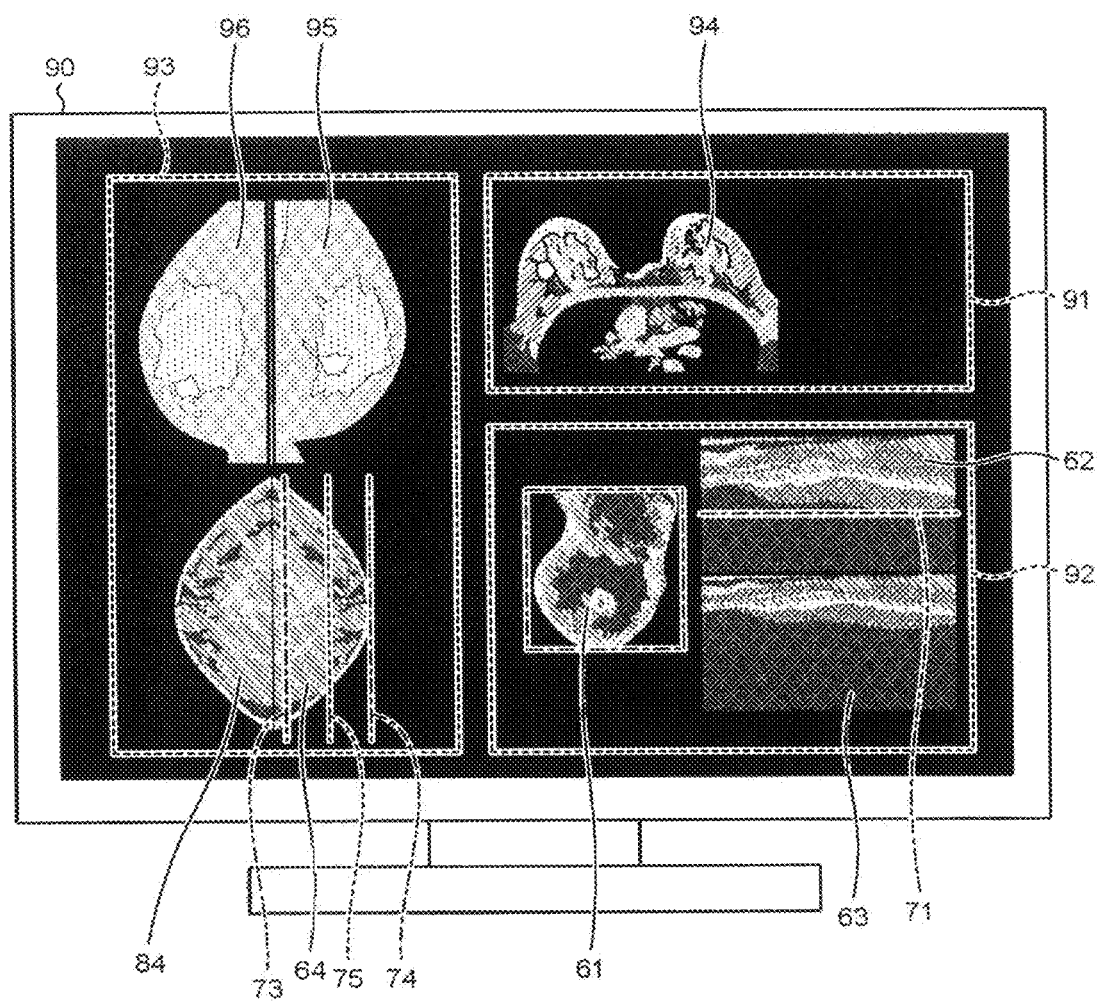
FIG. 23 is a diagram illustrating another example of a display of sectional images realized by a display control unit according to yet another embodiment.

FIG. 23 is a diagram illustrating another example of a display of sectional images realized by a display control unit according to yet another embodiment. In the present embodiment, a general-purpose monitor 90 that is viewed at conferences or training sessions is used as the display. In this situation, for example, the general-purpose monitor 90 is a monitor of which the resolution level is not as high as the resolution levels of monitors approved for medical use, but is higher than the resolution levels of commonly-used monitors installed with a personal computer or the like. For example, the general-purpose monitor 90 in this situation may be configured by using a high-resolution monitor such as a so-called 4K or 8K monitor that is recently becoming popular.

For example, as illustrated in FIG. 23, in the display area of the general-purpose monitor 90, the display control unit displays a plurality of medical images imaging mutually the same subject, in response to an instruction from the operator. For example, the display control unit displays a Magnetic Resonance (MR) image in an area 91 in the top right position as viewed from the operator, displays ultrasonic images in an area 92 in the bottom right position, and displays mammography images in an area 93 in the left position.

For example, the display control unit displays an axial image 94 of the MR image in the area 91. Further, the display control unit displays the coronal image 61, the axial image 62, and the sagittal image 63 of the ultrasonic images in the area 92. In addition, the display control unit displays Mediolateral Oblique (MLO) images and CC images of the mammography images in the area 93. For example, in an upper section of the area 93, the display control unit displays an MLO image 95 of the left breast and an MLO image 96 of the right breast that are positioned next to each other. Further, for example, in a lower section of the area 93, the display control unit displays a CC image 64 of the left breast and a CC image 84 of the right breast that are positioned next to each other.

Further, in the same manner as in the embodiment described above, in the axial image 62 of the ultrasonic image, the display control unit displays the line 71 indicating the position of the chest wall detected by the first detection unit. Further, in the CC image 64 of the mammography image, the display control unit displays the line 73 indicating the position of the chest wall detected by the second detection unit and the line 74 indicating the position of the nipple detected by the second detection unit. In addition, in the CC image 64 of the mammography image, the display control unit displays the line 75 indicating the position of the coronal image 61 of the ultrasonic image.

After that, in the same manner as in the embodiment described above, the display control unit displays the coronal image 61 of the ultrasonic image in conjunction with the line 75 displayed in the CC image 64 of the mammography image, in response to an operation accepted from the operator.

According to the present embodiment, for example, it is possible to easily grasp the positional relation among the images, when a discussion is held at a conference or a training session, while using the medical images imaged by the plurality of medical image diagnostic apparatuses. As a result, it is possible to more appropriately discuss medical examination plans and treatment plans.

Although the above embodiment describes the example in which the ultrasonic image is displayed on the first monitor 81, whereas the mammography image of the right breast is displayed on the second monitor 82, and the mammography image of the left breast is displayed on the third monitor 83, possible embodiments are not limited to this example. For instance, mammography images of both the left and the right breasts may be displayed on a single monitor. Further, an ultrasonic image or an MR image may be displayed on the monitor used for displaying mammography images.

Further, the above embodiment describes an example that uses the MR image; however, the medical image referred to together with the ultrasonic images and the mammography images does not necessarily have to be an MR image. For example, any of various types of medical images imaged by other medical image diagnostic apparatuses, such as a Computed Tomography (CT) image imaged by an X-ray CT apparatus or a Positron Emission Tomography (PET) image imaged by a PET apparatus, may be referred to.

Further, the above embodiment describes the example in which the display control unit accepts the operation performed on the coronal image 61 or the CC image 64, via the input device; however, possible embodiments are not limited to this example. For instance, at a conference or a training session, it is acceptable to accept the operation performed on the coronal image 61 or the axial image 64, via a tablet terminal that displays, in synchronization, the same screen as the one displayed on the general-purpose monitor 90.

Figure 24:
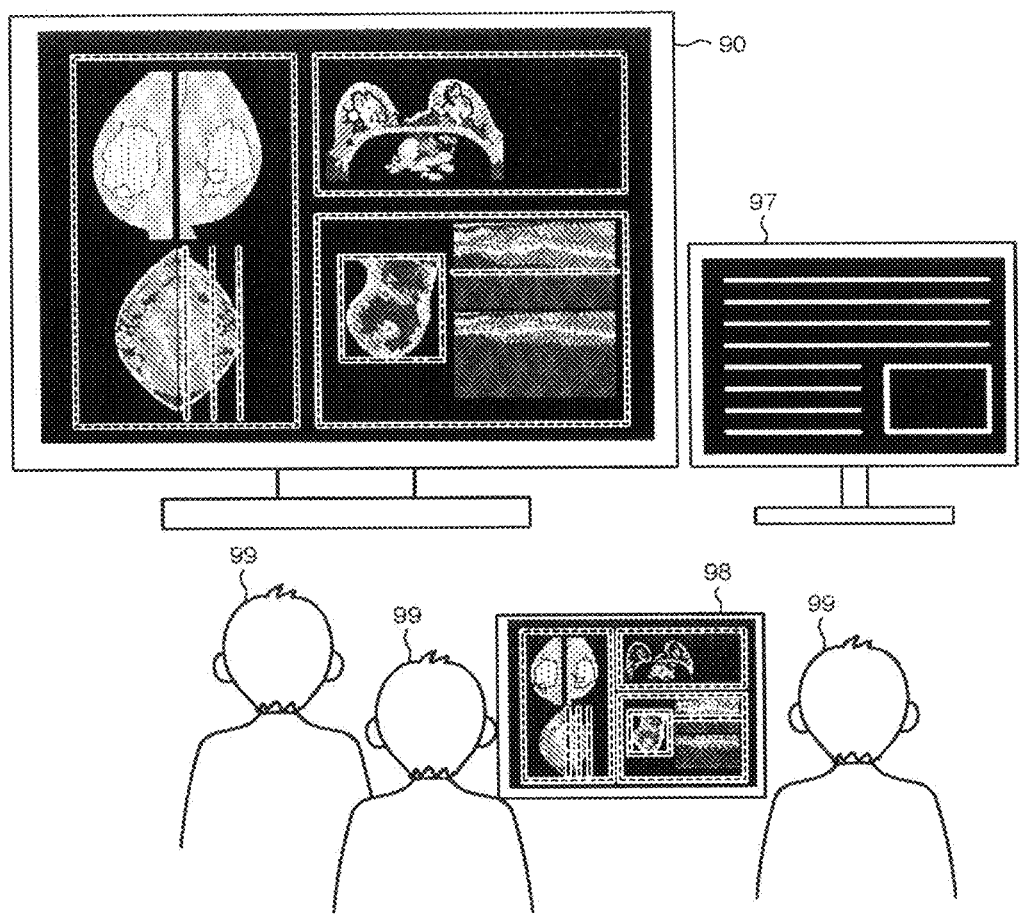
FIG. 24 is a diagram illustrating another example of accepting an operation performed on sectional images according to yet another embodiment.

FIG. 24 is a diagram illustrating another example of accepting an operation performed on sectional images according to yet another embodiment. For example, as illustrated in FIG. 24, in the present embodiment, the medical image processing apparatus displays images of a subject imaged by various types of medical image diagnostic apparatuses on the general-purpose monitor 90, in the same manner as in the embodiment described above. For example, as illustrated in FIG. 24, at a conference, a monitor 97 that displays an image interpretation report may be used, in addition to the general-purpose monitor 90 that displays the medical images of the subject.

In this situation, the medical image processing apparatus displays the images, the GUI, and the like that are displayed in the display area of the general-purpose monitor 90, also on a tablet terminal 98 in the same display manner and in synchronization therewith. For example, the medical image processing apparatus and the tablet terminal 98 are connected to each other via a wired or wireless network.

Further, at a conference, a plurality of medical doctors 99 discuss medical examination plans and treatment plans, while referring to the plurality of medical images displayed on the general-purpose monitor 90 and the tablet terminal 98 as well as an image interpretation report or the like displayed on the monitor 97. In that situation, for example, the display control unit accepts an operation performed by an operator on the CC image 64 or the coronal image 61 via the input device included therein and also accepts a similar operation via the tablet terminal 98.

More specifically, in the display area of the tablet terminal 98, the display control unit displays the same contents as those displayed in the display area of the general-purpose monitor 90 in synchronization therewith. Also, in the display area of the tablet terminal 98, the display control unit accepts an operation to move the line 75 displayed in the CC image 64 of the mammography image in the direction toward the chest wall or in the direction toward the nipple. Further, in the display area of the tablet terminal 98, the display control unit accepts an operation to replace the coronal image 61 of the ultrasonic image, with a coronal image corresponding to another position generated from the same volume data. Further, in the same manner as in the embodiment described above, the medical image processing apparatus causes the coronal image of the ultrasonic image to be displayed in conjunction with the line 75 displayed in the CC image 64 of the mammography image, on the general-purpose monitor 90 and on the tablet terminal 98, in response to an operation accepted via the tablet terminal 98.

According to the present embodiment, for example, at a conference or a training session, a medical doctor who operates the tablet terminal 98 is able to easily change what is displayed on the general-purpose monitor 90. As a result, it is possible to discuss medical examination plans and treatment plans more efficiently.

Although the above embodiment describes the example that uses the tablet terminal 98, possible embodiments are not limited to this example. For instance, instead of the tablet terminal 98, a notebook or desktop personal computer connected to the medical image processing apparatus via a wired or wireless network may be used.

Although the above embodiment describes an example of a case in which the second piece of image data is the three-dimensional mammography image data, possible embodiments are not limited to this example. The second piece of image data may be two-dimensional medical image data obtained by imaging a breast of a subject. Further, for example, although the above embodiment describes an example of a case in which the second generating unit generates the second sectional image based on the second volume data as the three-dimensional mammography image data, the mammography image data may be two-dimensional mammography images; in that case, the second generating unit uses the two-dimensional mammography image data obtained by imaging the breast of the subject by the mammography apparatus 10 as the second sectional image as it is.

Further, although the above embodiment describes the example in which the first piece of image data represented by the three-dimensional medical image data is the three-dimensional ultrasonic images, possible embodiments are not limited to this example. The first piece of image data may be three-dimensional medical image data obtained by imaging a breast of a subject by using another medical image diagnostic apparatus. For example, the first piece of image data may be three-dimensional MR image data obtained by imaging a breast of a subject by using a Magnetic Resonance Imaging (MRI) apparatus. Alternatively, the first piece of image data may be Computed Tomography (CT) image data imaged by an X-ray CT apparatus, or a Positron Emission Tomography (PET) image imaged by a PET apparatus.

Although the above embodiment describes an example of a case in which the second piece of image data is the three-dimensional mammography image data, that is not limiting; the second piece of image data may be medical image data obtained by imaging a breast of a subject by using another medical image diagnostic apparatus. For example, the second piece of image data may be MR image data imaged by an MRI apparatus, CT image data imaged by an X-ray CT apparatus, or a PET image imaged by a PET apparatus.

Images of breasts generally differ in the direction and shape of a breast on an image by the type of the medical image diagnostic apparatus that performs imaging. For example, the MRI apparatus performs imaging with a subject laid face down, and the breast on the image is directed downward. The MRI apparatus installs a receiving RF coil on the breast of the subject. Unlike the mammography apparatus, the RF coil does not pressurize the breast, and imaging is performed without the breast being flattened. The X-ray CT apparatus often performs imaging with the subject laid face up or face down, whereas the PET apparatus often performs imaging with the subject directed downward. In some cases, the PET apparatus performs imaging with the breast pressurized as in the mammography apparatus.

Meanwhile, because the method described in the above embodiment associates the positional relation of the breast based on the positions of the cheat wall and the nipple detected in the pieces of image data, even when mammary gland image diagnosis is performed by using, in combination, pieces of image data that differ in the direction or shape of the breast in the images, the positional relation of the breast can be easily associated between the two pieces of image data. As a result, it is possible to perform the mammary gland image diagnosis by using various types of medical image data of the breast in combination.

The functions of the controllers described in the above embodiments can be implemented by respective pieces of software. For example, the functions of the controllers can be implemented by causing a computer to execute a medical image processing program that prescribes the procedures of the processing described as being performed by the respective controllers. In this case, the medical image processing program can be stored in, for example, a hard disk or a semiconductor memory device, is read by a processor such as a CPU and an MPU, and is executed. The medical image processing program can be recorded and provided in a computer-readable recording medium such as a compact disc-read only memory (CD-ROM), a magnetic optical (MO) disk, and a digital versatile disc (DVD).

The medical image processing apparatus, the medical image diagnostic apparatus, and the method for processing a medical image according to at least one embodiment described above can reduce a load related to interpretation in mammary gland image diagnosis using various types of medical image data in combination.

A report has been recently known that using a mammography apparatus for examinations for breast cancer can reduce a rate of requiring close examination and a false positive rate. In addition to this, the above embodiments can interpret ultrasonic images based on objective positional information, and a biopsy rate can be expected to be reduced in particular in the rate of requiring close examination.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   processing circuitry configured to:
   analyze a first piece of image data obtained by imaging a breast of a subject and a second piece of image data obtained by imaging the breast, and detect positions of a chest wall and a nipple in each of the pieces of image data, wherein the first piece of image data and the second piece of image data are three-dimensional medical image data and are obtained by different types of medical image diagnostic apparatuses,
   generate a first sectional image based on the first piece of image data and generate a second sectional image based on the second piece of image data,
   associate a positional relation of the breast in the first piece of image data and the second piece of image data so that the positions of the chest wall and the nipple match between the first and the second pieces of image data, and
   display on a display the first sectional image, the second sectional image, and a mark indicating the position of the first piece of image data on the second piece of image data.

2. The medical image processing apparatus according to claim 1, wherein, with respect to at least one piece of the first and the second pieces of image data, the processing circuitry is further configured to detect the position of the chest wall in the at least one piece of image data by threshold processing based on a distribution of brightness values of voxels contained in the at least one piece of image data.

3. The medical image processing apparatus according to claim 1, wherein, with respect to at least one piece of the first and the second pieces of image data, the processing circuitry is further configured to detect the position of the chest wall in the at least one piece of image data by a method of differential edge detection based on a distribution of brightness values of voxels contained in the at least one piece of image data.

4. The medical image processing apparatus according to claim 1, wherein, with respect to at least one piece of the first and the second pieces of image data, the processing circuitry is further configured to detect the position of the chest wall in the at least one piece of image data by a Sobel operator based on a distribution of brightness values of voxels contained in the at least one piece of image data.

5. The medical image processing apparatus according to claim 1, wherein, with respect to at least one piece of the first and the second pieces of image data, the processing circuitry is further configured to detect a position of a coronal image closest to a body surface in the at least one piece of image data as the position of the nipple in the at least one piece of image data.

6. The medical image processing apparatus according to claim 1, wherein, with respect to at least one of the first and the second pieces of image data, the processing circuitry is further configured to detect a position of a coronal image closest to a thoracic cavity in the at least one piece of image data as the position of the chest wall in the at least one piece of image data.

7. The medical image processing apparatus according to claim 1, wherein, with respect to at least one of the first and the second pieces of image data, the processing circuitry is further configured to conduct a search in brightness values of voxels contained in the at least one piece of image data, starting with a side opposite a thoracic cavity, and detect a position whose brightness value has first exceeded a certain threshold as the position of the nipple in the at least one piece of image data.

8. The medical image processing apparatus according to claim 1, wherein the first piece of image data is ultrasonic image data.

9. The medical image processing apparatus according to claim 1, wherein the first piece of image data is magnetic resonance (MR) image data.

10. A medical image processing apparatus comprising:
processing circuitry configured to:
analyze a first piece of image data obtained by imaging a breast of a subject and a second piece of image data obtained by imaging the breast, and detect positions of a chest wall and a nipple in each of the pieces of image data, wherein the first piece of image data and the second piece of image data are three-dimensional medical image data and are obtained by different types of medical image diagnostic apparatuses,
generate a first sectional image based on the first piece of image data and generates a second sectional image based on the second piece of image data, and
associate a positional relation of the breast in the first piece of image data and the second piece of image data so that the positions of the chest wall and the nipple match between the first and the second pieces of image data, wherein the processing circuitry is further configured to generate the first sectional image and the second sectional image corresponding to a mutually same position based on the positional relation of the breast.

11. The medical image processing apparatus according to claim 10, wherein, with respect to at least one piece of the first and the second pieces of image data, the processing circuitry is further configured to detect the position of the chest wall in the at least one piece of image data by threshold processing based on a distribution of brightness values of voxels contained in the at least one piece of image data.

12. The medical image processing apparatus according to claim 10, wherein, with respect to at least one piece of the first and the second pieces of image data, the processing circuitry is further configured to detect the position of the chest wall in the at least one piece of image data by a method of differential edge detection based on a distribution of brightness values of voxels contained in the at least one piece of image data.

13. The medical image processing apparatus according to claim 10, wherein, with respect to at least one piece of the first and the second pieces of image data, the processing circuitry is further configured to detect the position of the chest wall in the at least one piece of image data by a Sobel operator based on a distribution of brightness values of voxels contained in the at least one piece of image data.

14. The medical image processing apparatus according to claim 10, wherein, with respect to at least one piece of the first and the second pieces of image data, the processing circuitry is further configured to detect a position of a coronal image closest to a body surface in the at least one piece of image data as the position of the nipple in the at least one piece of image data.

15. The medical image processing apparatus according to claim 10, wherein, with respect to at least one of the first and the second pieces of image data, the processing circuitry is further configured to detect a position of a coronal image closest to a thoracic cavity in the at least one piece of image data as the position of the chest wall in the at least one piece of image data.

16. The medical image processing apparatus according to claim 10, wherein, with respect to at least one of the first and the second pieces of image data, the processing circuitry is further configured to conduct a search in brightness values of voxels contained in the at least one piece of image data, starting with a side opposite a thoracic cavity, and detect a position whose brightness value has first exceeded a certain threshold as the position of the nipple in the at least one piece of image data.

17. A medical image diagnostic apparatus comprising:
processing circuitry configured to:
analyze a first piece of image data obtained by imaging a breast of a subject and a second piece of image data obtained by imaging the breast, and detect positions of a chest wall and a nipple in each of the pieces of image data, wherein the first piece of image data and the second piece of image data are three-dimensional medical image data and are obtained by different types of medical image diagnostic apparatuses,
generate a first sectional image based on the first piece of image data and generates a second sectional image based on the second piece of image data,
associate a positional relation of the breast in the first piece of image data and the second piece of image data so that the positions of the chest wall and the nipple match between the first and the second pieces of image data, and display on a display the first sectional image, the second sectional image, and a mark indicating the position of the first piece of image data on the second piece of image data.

* * * * *